United States Patent
Arai et al.

(10) Patent No.: US 8,409,074 B2
(45) Date of Patent: Apr. 2, 2013

(54) SLEEPING STATE IMPROVEMENT SYSTEM AND SLEEPING STATE IMPROVEMENT METHOD

(75) Inventors: Junichiro Arai, Kusatsu (JP); Katsuya Miura, Osaka (JP); Takayuki Ishiwata, Kusatsu (JP); Masahiro Tanaka, Sakai (JP)

(73) Assignee: Daikin Industries, Ltd., Osaka (JP)

( * ) Notice: Subject to any disclaimer, the term of this patent is extended or adjusted under 35 U.S.C. 154(b) by 1131 days.

(21) Appl. No.: 11/663,459

(22) PCT Filed: Sep. 14, 2005

(86) PCT No.: PCT/JP2005/016920
§ 371 (c)(1),
(2), (4) Date: Mar. 22, 2007

(87) PCT Pub. No.: WO2006/038441
PCT Pub. Date: Apr. 13, 2006

(65) Prior Publication Data
US 2008/0146866 A1    Jun. 19, 2008

(30) Foreign Application Priority Data
Oct. 4, 2004  (JP) .................................. 2004-291359

(51) Int. Cl.
*A61M 21/00* (2006.01)
(52) U.S. Cl. ........................................ 600/27; 600/534
(58) Field of Classification Search ............... 600/26–28; 128/897–898
See application file for complete search history.

(56) References Cited

U.S. PATENT DOCUMENTS

| | | | |
|---|---|---|---|
| 5,435,147 A | 7/1995 | Mochizuki et al. | |
| 5,441,476 A | 8/1995 | Kitado et al. | |
| 2004/0153344 A1 | 8/2004 | Bui et al. | |
| 2005/0143617 A1* | 6/2005 | Auphan .................. | 600/26 |

FOREIGN PATENT DOCUMENTS

| | | |
|---|---|---|
| DE | 100 24 103 A1 | 11/2001 |
| JP | 02-154767 A | 6/1990 |
| JP | 04-300507 A | 10/1992 |
| JP | 05-015598 A | 1/1993 |
| JP | 05-146512 A | 6/1993 |
| JP | 11-244383 A | 9/1999 |
| JP | 2002-288211 A | 10/2002 |
| JP | 2003-120989 A | 4/2003 |
| JP | 2003-164496 A | 6/2003 |
| JP | 2003-339674 A | 12/2003 |
| WO | WO 2004/032719 A2 | 4/2004 |
| WO | WO 2004/075714 A2 | 9/2004 |

OTHER PUBLICATIONS

European Search Report of corresponding EP Application. No. 05 78 3210.7 dated Jul. 2, 2012.

* cited by examiner

*Primary Examiner* — Charles A Marmor, II
*Assistant Examiner* — Carrie R Dorna
(74) *Attorney, Agent, or Firm* — Global IP Counselors

(57) ABSTRACT

A sleeping state improvement system to improve a sleeping state of a user includes a memory device and a control device that comprises a specification unit and a control unit. The memory device can be carried by the user. The specification unit specifies individual attribute information of the user based on individual information. The individual information is information stored in the memory device. The control unit controls an environment during sleep of the user based on the individual attribute information.

17 Claims, 12 Drawing Sheets

SLEEPING STATE IMPROVEMENT SYSTEM AND SLEEPING STATE IMPROVEMENT METHOD

CROSS-REFERENCE TO RELATED APPLICATIONS

This U.S. National stage application claims priority under 35 U.S.C. §119(a) to Japanese Patent Application No. 2004-291359, filed in Japan on Oct. 4, 2004, the entire contents of which are hereby incorporated herein by reference.

TECHNICAL FIELD

The present invention relates to a sleeping state improvement system and a sleeping state improvement method.

BACKGROUND ART

Conventionally, there is known a system that presumably determines a user's sleep stage and controls an air conditioner and the like (see JP-A Publication No. 2003-339674 (pages 1 to 11, FIGS. 1 to 19)).

SUMMARY OF THE INVENTION

Problem to be Solved by the Invention

However, with conventional techniques, there is a tendency that it is difficult to improve a sleeping state of a user when the user sleeps away from home. In other words, with conventional techniques, a device to presumably determine a sleep stage of a user is necessary in order to improve the sleeping state of the user, however, such a device to presumably determine the sleep stage is difficult to carry because of its size, weight, and the like. Consequently, such a device to presumably determine the sleep stage of a user can not be used in some cases when the user sleeps away from home, and therefore there is a tendency that it is difficult to improve the sleeping state of the user when the user sleeps away from home.

Therefore, it is an object of the present invention to provide a sleeping state improvement system and a sleeping state improvement method, which are capable of improving a sleeping state of a user even when the user sleeps away from home.

Means to Solve the Problem

A sleeping state improvement system according to a first aspect of the present invention is a sleeping state improvement system configured to improve a sleeping state of a user, comprising a memory member, a specification unit, and a control unit. The memory member can be carried by a user. The specification unit specifies individual attribute information of the user based on individual information. The individual information is information stored in the memory member. The control unit controls an environment during sleep of the user based on the individual attribute information.

With this sleeping state improvement system, the memory member can be carried by the user. The individual information can be read out from the memory member. The specification unit is capable of receiving the individual information. The specification unit specifies the individual attribute information of the user based on the individual information. The control unit is capable of receiving the individual attribute information. The control unit controls the environment during sleep of the user based on the individual attribute information.

Therefore, since the individual attribute information of the user is specified based on the individual information, the individual attribute information of the user can be specified even when the user sleeps away from home. In addition, since the environment during sleep of the user is controlled based on the individual attribute information, it is possible to control the environment during sleep according to individual difference of the user. Consequently, it is possible to improve the sleeping state of the user even when the user sleeps away from home.

A sleeping state improvement system according to a second aspect of the present invention is the sleeping state improvement system according to the first aspect of the present invention, further comprising a read-out device. The read-out device reads out the individual information from the memory member.

With this sleeping state improvement system, the memory member can be carried by the user. The read-out device reads out the individual information from the memory member. The specification unit is capable of receiving the individual information. The specification unit specifies the individual attribute information of the user based on the individual information. The control unit is capable of receiving the individual attribute information. The control unit controls the environment during sleep of the user based on the individual attribute information.

Therefore, since the individual attribute information of the user is specified based on the individual information, it is possible to specify the individual attribute information of the user even when the user sleeps away from home. In addition, since the environment during sleep of the user is controlled based on the individual attribute information, it is possible to control the environment during sleep according to individual difference of the user. Consequently, it is possible to improve the sleeping state of the user even when the user sleeps away from home.

A sleeping state improvement system according to a third aspect of the present invention is the sleeping state improvement system according to the first aspect or the second aspect of the present invention, wherein the individual information includes the individual attribute information of the user.

With this sleeping state improvement system, the memory member can be carried by the user. The individual information can be read out from the memory member. The individual information includes the individual attribute information of the user. The specification unit is capable of receiving the individual information. The specification unit specifies the individual attribute information of the user based on the individual information. The control unit is capable of receiving the individual attribute information. The control unit controls the environment during sleep of the user based on the individual attribute information.

Therefore, since the individual information includes the individual attribute information of the user, it is possible to read out the individual attribute information from the memory member and control the environment during sleep of the user based on the individual attribute information.

A sleeping state improvement system according to a fourth aspect of the present invention is the sleeping state improvement system according to the first aspect of the present invention, further comprising a read-out device and a management device. The read-out device reads out the individual information from the memory member. The management device stores the individual attribute information for each user. The individual information includes identification information. The identification information is information to identify the user. The read-out device transmits the identification information to the management device via a network. The management device transmits the individual attribute information of the user to the read-out device via the network.

With this sleeping state improvement system, the memory member can be carried by the user. The read-out device reads out the individual information from the memory member. The individual information includes the identification information. The identification information can be specified based on the individual information. The read-out device transmits the identification information to the management device via the network. The management device is capable of receiving the identification information from the read-out device via the network. The specification unit is capable of receiving the individual information. The management device stores the individual attribute information for each user. The specification unit is capable of referring to the individual attribute information stored in the management device. The specification unit specifies the individual attribute information of the user based on the identification information. The management device transmits the individual attribute information of the user to the read-out device via the network. The read-out device is capable of receiving the individual attribute information of the user from the management device via the network. The control unit is capable of receiving the individual attribute information of the user from the read-out device. The control unit controls the environment during sleep of the user based on the individual attribute information.

Therefore, since the individual attribute information is stored in the management device, it is possible to save the memory capacity in the memory member. In addition, since the individual attribute information is stored in the management device, it is possible to lower the burden of the user to manage the individual attribute information.

A sleeping state improvement system according to a fifth aspect of the present invention is the sleeping state improvement system according to any one of the first aspect to the fourth aspect of the present invention, further comprising an input unit. The individual attribute information is input to the input unit.

With this sleeping state improvement system, the memory member can be carried by the user. The individual attribute information is input to the input unit. The individual attribute information can be stored in the memory member or in a different device. The individual information can be read out from the memory member. The specification unit is capable of receiving the individual information. The specification unit specifies the individual attribute information of the user based on the individual information. The control unit is capable of receiving the individual attribute information. The control unit controls the environment during sleep of the user based on the individual attribute information.

Therefore, since the individual attribute information is input, it is possible to store the individual attribute information of the user and specify the individual attribute information of the user based on the individual information.

A sleeping state improvement system according to a sixth aspect of the present invention is the sleeping state improvement system according to the fifth aspect of the present invention, wherein the individual attribute information includes at least one of the following: age, sex, degree of obesity, physical condition, and race of the user.

With this sleeping state improvement system, the memory member can be carried by the user. The individual attribute information is input to the input unit. The individual attribute information includes at least one of the following: age, sex, degree of obesity, physical condition, and race of the user. The individual attribute information can be stored. The individual information can be read out from the memory member. The specification unit is capable of receiving the individual information. The specification unit specifies the individual attribute information of the user based on the individual information. The control unit is capable of receiving the individual attribute information. The control unit controls the environment during sleep of the user based on the individual attribute information.

Therefore, since the individual attribute information can be used as static information, it is possible to control the environment during sleep according to the static information of the user.

A sleeping state improvement system according to a seventh aspect of the present invention is the sleeping state improvement system according to any one of the first aspect to the sixth aspect of the present invention, further comprising a detection unit. The detection unit detects sleep onset of the user based on the biological information. The biological information is information regarding at least one of following: body movement, heartbeat, and breathing of the user.

With this sleeping state improvement system, the memory member can be carried by the user. The individual information can be read out from the memory member. The specification unit is capable of receiving the individual information. The specification unit specifies the individual attribute information of the user based on the individual information. The control unit is capable of receiving the individual attribute information. The detection unit detects sleep onset of the user based on the biological information. The control unit is capable of receiving information regarding sleep onset of the user. The control unit controls the environment during sleep of the user based on the individual attribute information.

Therefore, since sleep onset of the user is detected based on the biological information, it is possible to determine the timing to start controlling the environment during sleep of the user.

A sleeping state improvement system according to an eighth aspect of the present invention is the sleeping state improvement system according to the seventh aspect of the present invention, further comprising a detection unit. The detection unit further detects the individual attribute information based on the biological information.

With this sleeping state improvement system, the memory member can be carried by the user. The detection unit detects sleep onset of the user based on the biological information. The detection unit further detects the individual attribute information based on the biological information. The individual attribute information can be stored in the memory member or in a different device. The individual information can be read out from the memory member. The specification unit is capable of receiving the individual information. The specification unit specifies the individual attribute information of the user based on the individual information. The control unit is capable of receiving the individual attribute information. The detection unit detects sleep onset of the user based on the biological information. The control unit is capable of receiving information regarding sleep onset of the user. The control unit controls the environment during sleep of the user based on the individual attribute information.

Therefore, since the individual attribute information is detected, it is possible to store the individual attribute information of the user and specify the individual attribute information of the user based on the individual information.

A sleeping state improvement system according to a ninth aspect of the present invention is the sleeping state improvement system according to the eighth aspect of the present invention, wherein the detection unit detects the individual attribute information by detecting sleep onset of the user and sleep offset of the user, based on the biological information. The individual attribute information includes at least either one of the following: average sleep duration of the user and the sleep duration of the user during a previous predetermined period of time.

With this sleeping state improvement system, the memory member can be carried by the user. The individual information can be read out from the memory member. The specification unit is capable of receiving the individual information. The detection unit detects the individual attribute information based on the biological information. The detection unit detects the individual attribute information by detecting sleep onset of the user and sleep offset of the user based on the biological information. The individual attribute information includes at least one of the following: average sleep duration of the user and the sleep duration of the user during a previous predetermined period of time. The specification unit is capable of receiving the individual information. The specification unit specifies the individual attribute information of the user based on the individual information. The control unit is capable of receiving the individual attribute information. The control unit controls the environment during sleep of the user based on the individual attribute information.

Therefore, since the individual attribute information includes the average sleep duration of the user and the like, it is possible to control the environment during sleep according to individual difference such as the average sleep duration of the user and the like.

A sleeping state improvement system according to a tenth aspect of the present invention is the sleeping state improvement system according to the second aspect of the present invention, wherein the control unit presumably determines that the user has reached sleep onset based on that the read-out device read out the individual information.

With this sleeping state improvement system, the memory member can be carried by the user. The read-out device reads out the individual information from the memory member. The individual information is the individual attribute information of the user. The specification unit is capable of receiving the individual information. The specification unit specifies the individual attribute information of the user based on the individual information. The control unit is capable of receiving the individual attribute information. The control unit presumably determines that the user has reached sleep onset based on that the read-out device read out the individual information. The control unit controls the environment during sleep of the user based on the individual attribute information.

Therefore, since the control unit presumably determines that the user has reached sleep onset based on that the read-out device read out the individual information, it is possible to control the environment during sleep of the user even when the user sleeps away from home and sleep onset cannot be detected.

A sleeping state improvement system according to an eleventh aspect of the present invention is the sleeping state improvement system according to the fourth aspect of the present invention, wherein the control unit presumably determines that the user has reached sleep onset based on that the read-out device received the individual attribute information via the network.

With this sleeping state improvement system, the memory member can be carried by the user. The read-out device reads out the identification information from the memory member. The management device stores the individual attribute information for each user. The read-out device transmits the identification information to the management device via the network. The management device is capable of receiving the identification information from the read-out device via the network. The specification unit is capable of receiving the identification information. The specification unit specifies the individual attribute information of the user based on the identification information. The management device transmits the individual attribute information of the user to the read-out device via the network. The read-out device is capable of receiving the individual attribute information of the user from the management device via the network. The control unit presumably determines that the user has reached sleep onset based on that the read-out device received the individual attribute information via the network. The control unit controls the environment during sleep of the user based on the individual attribute information.

Therefore, since the control unit presumably determines that the user has reached sleep onset based on that the read-out device received the individual attribute information via the network, even when the user sleeps away from home and sleep onset of user cannot be detected, it is possible to control the environment during sleep of the user.

A sleeping state improvement system according to a twelfth aspect of the present invention is the sleeping state improvement system according to any one of the seventh aspect to the eleventh aspect of the present invention, wherein the environment refers to the ambient temperature of the user. The control unit gradually lowers the temperature over a first predetermined period of time from sleep onset of the user, and gradually raises the temperature over a second predetermined period of time until sleep offset of the user.

With this sleeping state improvement system, the detection unit detects sleep onset of the user based on the biological information. Alternatively, the control unit presumably determines that the user has reached sleep onset based on that the read-out device read out the individual information. Alternatively, the control unit presumably determines that the user has reached sleep onset based on that the read-out device received the individual attribute information via the network. Further, the control unit is capable of presumably determining the expected wake up time of the user. The control unit gradually lowers the temperature over the first predetermined period of time from sleep onset of the user, and gradually raises the temperature over the second predetermined period of time until sleep offset of the user.

Therefore, since the control unit gradually lowers the temperature over the first predetermined period of time from sleep onset of the user, and gradually raises the temperature over the second predetermined period of time until sleep offset of the user, it is possible to control the temperature during sleep of the user so that the temperature fits the biological rhythm.

A sleeping state improvement system according to a thirteenth aspect of the present invention is the sleeping state improvement system according to the eighth aspect of the present invention, wherein the individual attribute information includes at least one of following: sleep depth, body temperature, average sleep duration of the user, and sleep duration of the user during a previous predetermined period of time.

With this sleeping state improvement system, the memory member can be carried by the user. The individual information can be read out from the memory member. The specification unit is capable of receiving the individual information.

The detection unit detects the individual attribute information based on the biological information. The individual attribute information includes at least one of the following: sleep depth, body temperature, average sleep duration of the user, and sleep duration of the user during a previous predetermined period of time. The specification unit is capable of receiving the individual information. The specification unit specifies the individual attribute information of the user based on the individual information. The control unit is capable of receiving the individual attribute information. The control unit controls the environment during sleep of the user based on the individual attribute information.

Therefore, since the individual attribute information can be used as dynamic information, it is possible to control the environment during sleep according to the dynamic information of the user.

A sleeping state improvement system according to a fourteenth aspect of the present invention is the sleeping state improvement system according to any one of the first aspect to the thirteenth aspect of the present invention, wherein the control unit controls the environment during sleep of the user by controlling an air conditioner. The environment refers to an air-conditioned environment. The air-conditioned environment refers to at least one of the following: temperature of air-conditioned air blown out from the air conditioner, humidity of air-conditioned air blown out from the air conditioner, flow direction of air-conditioned air blown out from the air conditioner, volume of air-conditioned air blown out from the air conditioner, cleanliness of air-conditioned air blown out from the air conditioner, and amount of ventilation provided by the air conditioner.

With this sleeping state improvement system, the memory member can be carried by the user. The individual information can be read out from the memory member. The specification unit is capable of receiving the individual information. The specification unit specifies the individual attribute information of the user based on the individual information. The control unit is capable of receiving the individual attribute information. The control unit controls the environment during sleep of the user based on the individual attribute information. The control unit controls the environment during sleep of the user by controlling the air conditioner. The environment refers to an air-conditioned environment. The air-conditioned environment refers to at least one of the following: temperature of air-conditioned air blown out from an air conditioner, humidity of air-conditioned air blown out from an air conditioner, flow direction of air-conditioned air blown out from an air conditioner, volume of air-conditioned air blown out from an air conditioner, cleanliness of air-conditioned air blown out from an air conditioner, and amount of ventilation provided by an air conditioner.

Therefore, since the air-conditioned environment during sleep of the user is controlled based on the individual attribute information, it is possible to control the air-conditioned environment during sleep according to individual difference of the user.

A sleeping state improvement method according to a fifteenth aspect of the present invention is a sleeping state improvement method to improve an sleeping state of the user, comprising a carrying step, a specification step, and a control step. In the carrying step, a memory member is carried by the user. In the specification step, the individual attribute information of the user is specified based on the individual information. The individual information is information stored in the memory member. In the control step, the environment during sleep of the user is controlled based on the individual attribute information.

With this sleeping state improvement method, the memory member is carried in the carrying step. In the specification step, the individual information can be read out from the memory member. In the specification step, the individual information can be received. In the specification step, the individual attribute information of the user is specified based on the individual information. In the control step, the individual attribute information can be received. In the control step, the environment during sleep of the user is controlled based on the individual attribute information.

Therefore, since the individual attribute information of the user is specified based on the individual information, even when the user sleeps away from home, it is possible to specify the individual attribute information of the user. In addition, since the environment during sleep of the user is controlled based on the individual attribute information, it is possible to control the environment during sleep according to individual difference of the user. Therefore, it is possible to improve the sleeping state of the user even when the user sleeps away from home.

Effect of the Invention

With the sleeping state improvement system according to the first aspect of the present invention, the individual attribute information of the user is specified based on the individual information, so that it is possible to specify the individual attribute information of the user even when the user sleeps away from home. In addition, since the environment during sleep of the user is controlled based on the individual attribute information, it is possible to control the environment during sleep according to individual difference of the user. Therefore, it is possible to improve the sleeping state of the user even when the user sleeps away from home.

With the sleeping state improvement system according to the second aspect of the present invention, the individual attribute information of the user is specified based on the individual information, so that it is possible to specify the individual attribute information of the user even when the user sleeps away from home. In addition, since the environment during sleep of the user is controlled based on the individual attribute information, it is possible to control the environment during sleep according to individual difference of the user. Consequently, it is possible to improve the sleeping state of the user even when the user sleeps away from home.

With the sleeping state improvement system according to the third aspect of the present invention, since the individual information includes the individual attribute information of the user, it is possible to read out the individual attribute information from the memory member and control the environment during sleep of the user based on the individual attribute information.

With the sleeping state improvement system according to the fourth aspect of the present invention, since the individual attribute information is stored in the management device, it is possible to save the memory capacity in the memory member. In addition, since the individual attribute information is stored in the management device, it is possible to lower the burden of the user to manage the individual attribute information.

With the sleeping state improvement system according to the fifth aspect of the present invention, since the individual attribute information is input, it is possible to store the individual attribute information of the user and specify the individual attribute information of the user based on the individual information.

With the sleeping state improvement system according to the sixth aspect of the present invention, since the individual attribute information can be used as static information, it is possible to control the environment during sleep according to the static information of the user.

With the sleeping state improvement system according to the seventh aspect of the present invention, since sleep onset of the user is detected based on the biological information, it is possible to determine the timing to start controlling the environment during sleep of the user.

With the sleeping state improvement system according to the eighth aspect of the present invention, since the individual attribute information is detected, it is possible to store the individual attribute information of the user and specify the individual attribute information of the user based on the individual information.

With the sleeping state improvement system according to the ninth aspect of the present invention, since the individual attribute information includes the average sleep duration of the user and the like, it is possible to control the environment during sleep according to individual difference such as the average sleep duration of the user and the like.

With the sleeping state improvement system according to the tenth aspect of the present invention, since the control unit presumably determines that the user has reached sleep onset based on that the read-out device read out the individual information, even when the user sleeps away from home and sleep onset of user cannot be detected, it is possible to control the environment during sleep of the user.

With the sleeping state improvement system according to the eleventh aspect of the present invention, since the control unit presumably determines that the user has reached sleep onset based on that the read-out device received the individual attribute information via the network, even when the user sleeps away from home and sleep onset of user cannot be detected, it is possible to control the environment during sleep of the user.

With the sleeping state improvement system according to the twelfth aspect of the present invention, since the control unit gradually lowers the temperature over the first predetermined period of time from sleep onset of the user, and gradually raises the temperature over the second predetermined period of time until sleep offset of the user, it is possible to control the temperature during sleep of the user so that the temperature fits the biological rhythm.

With the sleeping state improvement system according to the thirteenth aspect of the present invention, since the individual attribute information can be used as dynamic information, it is possible to control the environment during sleep according to the dynamic information of the user.

With the sleeping state improvement system according to the fourteenth aspect of the present invention, since the air-conditioned environment during sleep of the user is controlled based on the individual attribute information, it is possible to control the air-conditioned environment during sleep according to individual difference of the user.

With the sleeping state improvement method according to the fifteenth aspect of the present invention, since the individual attribute information of the user is specified based on the individual information, even when the user sleeps away from home, it is possible to specify the individual attribute information of the user. In addition, since the environment during sleep of the user is controlled based on the individual attribute information, it is possible to control the environment during sleep according to individual difference of the user. Therefore, it is possible to improve the sleeping state of the user even when the user sleeps away from home.

DETAILED DESCRIPTION OF THE PREFERRED EMBODIMENTS INVENTION

First Embodiment

Figure 1:
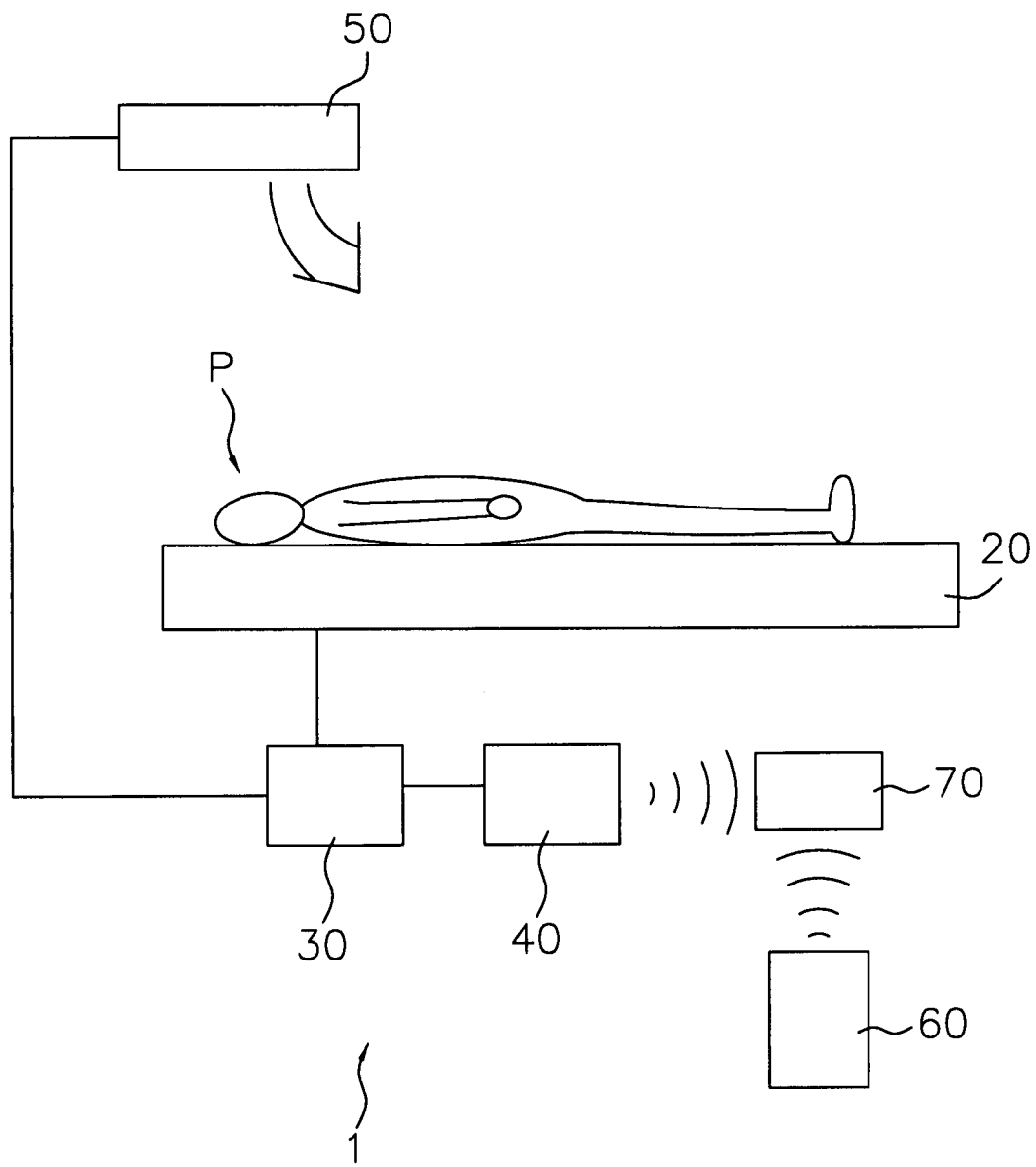
FIG. 1 is a schematic diagram of a sleeping state improvement system according to a first embodiment of the present invention.
Figure 2:
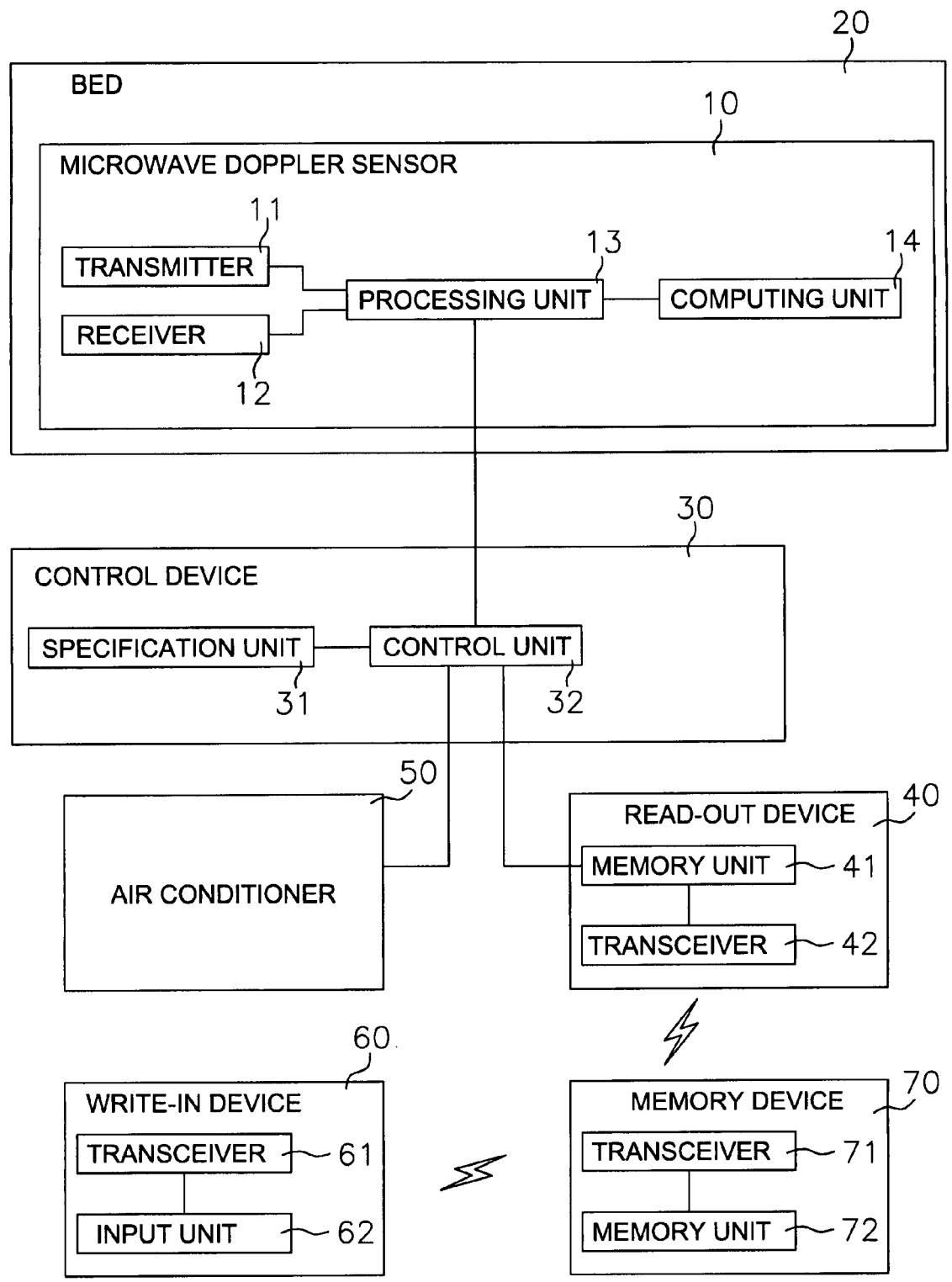
FIG. 2 is a block diagram of the sleeping state improvement system according to the first embodiment of the present invention.

FIG. 1 shows a schematic diagram of a sleeping state improvement system 1 according to a first embodiment of the present invention. In addition, FIG. 2 shows a block diagram of the sleeping state improvement system 1 according to the first embodiment of the present invention. The sleeping state improvement system 1 shown in FIG. 1 is a system configured to primarily improve a sleeping state of a user P.

<Overall Structure of the Sleeping State Improvement System 1>

As shown in FIG. 1, this sleeping state improvement system 1 mainly comprises a bed 20, a control device 30, a read-out device 40, an air conditioner 50, a write-in device 60, and a memory device 70. The user P sleeps on the bed 20. The bed 20, the control device 30, the read-out device 40, and the air conditioner 50 are provided in a room where the user P (see FIG. 1) sleeps away from home. The memory device 70 is carried by the user P (see FIG. 1) and brought to the room where the user P sleeps.

<Structure of the Write-In Device 60>

As shown in FIG. 2, the write-in device 60 shown in FIG. 1 mainly comprises a transceiver 61 and an input unit 62.

The individual attribute information is input to the input unit 62 shown in FIG. 2. Here, the individual attribute information is information regarding the age of the user P (see FIG. 1). The transceiver 61 receives the individual attribute information from the input unit 62 and sends the same to the memory device 70 via a wireless network. In other words, the individual attribute information is written into the memory device 70.

<Structure of the Memory Device 70>

As shown in FIG. 2, the memory device 70 shown in FIG. 1 mainly comprises a transceiver 71 and a memory unit 72. The memory device 70 can be carried by the user P (see FIG. 1). Here, the memory device 70 is an IC card.

The transceiver 71 shown in FIG. 2 receives the individual attribute information from the write-in device 60 via the wireless network. The memory unit 72 receives the individual attribute information from the transceiver 71 and stores the same. In other words, the individual attribute information is written into the memory device 70.

The transceiver 71 receives from the read-out device 40 via the wireless network a signal requiring reading out of the individual information, and receives the individual information from the memory unit 72 and sends the same to the read-out device 40 via the wireless network. Here, the individual information refers to the individual attribute information. In other words, the individual information is read out from the memory device 70.

<Structure of the Read-Out Device 40>

As shown in FIG. 2, the read-out device 40 shown in FIG. 1 mainly comprises a transceiver 42 and a memory unit 41.

The transceiver 42 shown in FIG. 2 sends the memory device 70 via the wireless network a signal requiring reading out of the individual information.

The transceiver 42 receives the individual information from the memory device 70 via the wireless network. In other words, the individual information is read out from the memory device 70. The memory unit 41 receives the individual information from the transceiver 42 and temporarily stores the same. The memory unit 41 sends the individual information to the control device 30.

<Structure of the Bed 20>

As shown in FIG. 2, the bed 20 shown in FIG. 1 mainly comprises a microwave Doppler sensor 10. The microwave Doppler sensor 10 mainly comprises a transmitter 11, a receiver 12, a processing unit 13, and a computing unit 14.

The transmitter 11 of the microwave Doppler sensor 10 shown in FIG. 2 transmits microwave to the user P (see FIG. 1). Note that microwave has characteristics to penetrate cloth, feather, artificial fiber, etc., which are materials of the bed 20 and clothing, and reflect off the body surface, the metal and the like. The receiver 12 receives a reflected wave. Here, the reflected wave is generated as a result of reflection of microwave from the body surface of the user P (see FIG. 1). In other words, the microwave Doppler sensor 10 obtains the microwave and reflected wave without contacting the user P (see FIG. 1). The computing unit 14 receives a microwave signal from the transmitter 11 via the processing unit 13. The computing unit 14 receives a reflected wave signal from the receiver 12 via the processing unit 13. The computing unit 14 computes change information. The change information is information regarding the change in the reflected wave signal with respect to the microwave signal. The computing unit 14 converts the change information to information regarding the amount of body movement. The processing unit 13 receives information regarding the amount of body movement from the computing unit 14 and sends the same to the control device 30.

<Structure of the Control Device 30>

As shown in FIG. 2, the control device 30 shown in FIG. 1 mainly comprises a control unit 32 and a specification unit 31.

The control unit 32 shown in FIG. 2 receives the individual information from the memory unit 41 of the read-out device 40. The specification unit 31 receives the individual information from the control unit 32, and specifies the individual attribute information based on the individual information. Here, the individual information is the individual attribute information. The control unit 32 receives the individual attribute information from the specification unit 31. The control unit 32 controls the environment during sleep of the user P (see FIG. 1) based on the individual attribute information.

Specifically, the control unit 32 determines the sleep duration of the user P (see FIG. 1) based on the individual attribute information. Here, the individual attribute information is information regarding the age of the user P (see FIG. 1). The control unit 32 receives information regarding the amount of body movement from the microwave Doppler sensor 10 of the bed 20. The control unit 32 determines whether or not the user P (see FIG. 1) falls asleep based on information regarding the amount of body movement. Or, the control unit 32 determines sleep onset of the user P (see FIG. 1) based on information regarding the amount of body movement. The control unit 32 refers to a timer (not shown) when determined that the user P (see FIG. 1) has reached sleep onset, and specifies the time of sleep onset. The control unit 32 presumably determines the expected wake up time of the user P (see FIG. 1) based on information regarding the sleep duration and time of sleep onset of the user P (see FIG. 1).

In addition, the control unit 32 generates a control signal to gradually lower the predetermined temperature over a first predetermined period of time (for example, three hours) from sleep onset of the user P (see FIG. 1), and sends the signal to the air conditioner 50. The control unit 32 generates a control signal to maintain the temperature after the first predetermined period of time has elapsed from sleep onset of the user P (see FIG. 1), and sends the signal to the air conditioner 50. The control unit 32 generates a control signal to gradually raise the maintained temperature over a second predetermined period of time (for example, three hours) until sleep offset of the user P (see FIG. 1), and sends the signal to the air conditioner 50. The control unit 32 causes a buzzer (not shown) or the like to sound an alarm at the expected wake up time of the user P (see FIG. 1), in order to wake up the user P (see FIG. 1).

<Structure of the Air Conditioner 50>

The air conditioner 50 shown in FIG. 1 is a typical air conditioner.

The air conditioner 50 receives from the control device 30 the control signal to gradually lower the predetermined temperature over the first predetermined period of time from sleep onset of the user P (see FIG. 1), and provides an air-conditioned environment around the user P (see FIG. 1) based on the control signal.

The air conditioner 50 receives from the control device 30 the control signal to maintain the temperature after the first predetermined period of time has elapsed from sleep onset of the user P (see FIG. 1), and provides an air-conditioned environment around the user P (see FIG. 1) based on the control signal.

The air conditioner 50 receives from the control device 30 the control signal to gradually raise the maintained temperature over the second predetermined period of time until sleep offset of the user P (see FIG. 1), and provides an air-conditioned environment around the user P (see FIG. 1) based on the control signal.

<Process Flow in Which the Sleeping State Improvement System 1 Improves the Sleeping State of the User P>

Figure 3:
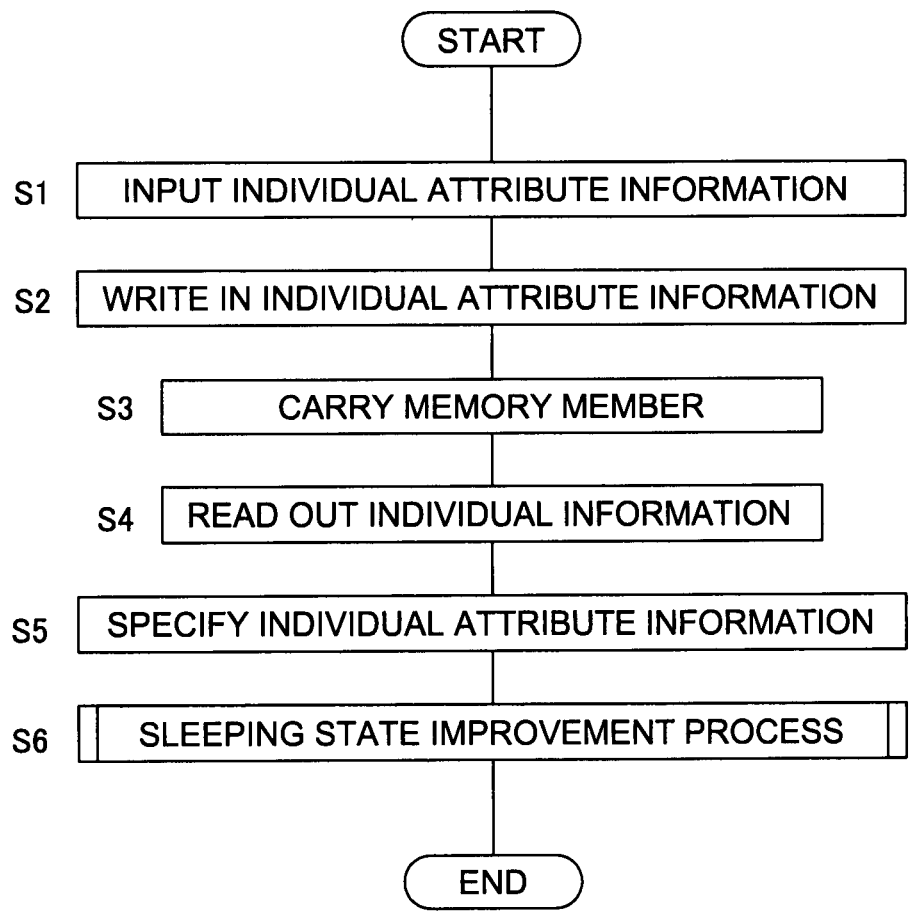
FIG. 3 is a flowchart showing a flow of a process in which the sleeping state improvement system improves a user's sleeping state.

A process flow in which the sleeping state improvement system 1 shown in FIG. 1 improves the sleeping state of the user P is described by using a flow chart shown in FIG. 3.

In step S1 shown in FIG. 3, the individual attribute information is input. In other words, the individual attribute information is input to the input unit 62 of the write-in device 60 shown in FIG. 2. Here, the individual attribute information is information regarding the age of the user P (see FIG. 1).

In step S2 shown in FIG. 3, the individual attribute information is written in. In other words, the transceiver 61 of the write-in device 60 shown in FIG. 2 receives the individual attribute information from the input unit 62 and sends the same to the memory device 70 via the wireless network. The transceiver 71 of the memory device 70 receives the individual attribute information from the write-in device 60 via the wireless network. The memory unit 72 receives the individual attribute information from the transceiver 71 and stores the same. In other words, the individual attribute information is written into the memory device 70.

In step S3 shown in FIG. 3, the memory device 70 is carried. In other words, by the user P shown in FIG. 1, the memory device 70 is carried and brought to the room away from home where the user P sleeps.

In step S4 shown in FIG. 3, the individual information is read out. In other words, the transceiver 42 of the read-out device 40 shown in FIG. 2 sends the signal requiring reading out of the individual information to the memory device 70 via the wireless network. Here, the individual information is the individual attribute information. The individual attribute information is information regarding the age of the user P (see FIG. 1). The transceiver 71 of the memory device 70 receives the signal requiring reading out of the individual information from the read-out device 40 via the wireless network, receives the individual information (individual attribute information) from the memory unit 72, and sends the same to the read-out device 40 via the wireless network. The transceiver 42 of the read-out device 40 receives the individual information (individual attribute information) from the memory device 70 via the wireless network. In other words, the individual information (individual attribute information) is read out from the memory device 70. The memory unit 41 receives the individual information (individual attribute information) from the transceiver 42 and temporarily stores the same.

In step S5 shown in FIG. 3, the individual attribute information is specified. In other words, the control unit 32 of the control device 30 shown in FIG. 2 receives the individual information (individual attribute information) from the memory unit 41 of the read-out device 40. The specification unit 31 receives the individual information (individual attribute information) from the control unit 32 and specifies the individual attribute information based on the individual information. Here, the individual information is the individual attribute information. The control unit 32 of the control device 30 receives the individual attribute information from the specification unit 31.

In step S6 shown in FIG. 3, the sleeping state improvement process is performed.

<Flow of the Sleeping State Improvement Process>

Figure 4:
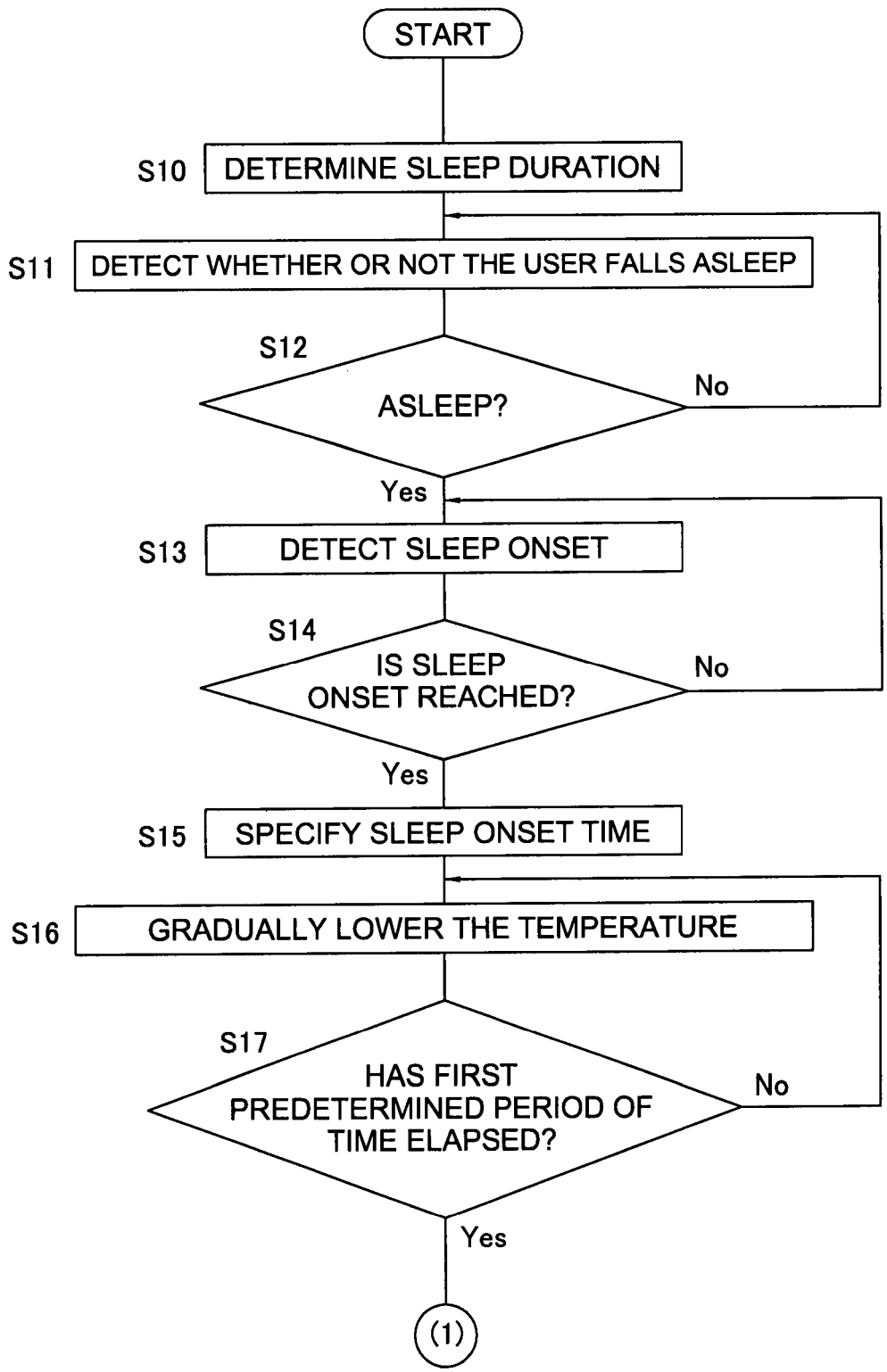
FIG. 4 is a flowchart showing a flow of a sleeping state improvement process.
Figure 5:
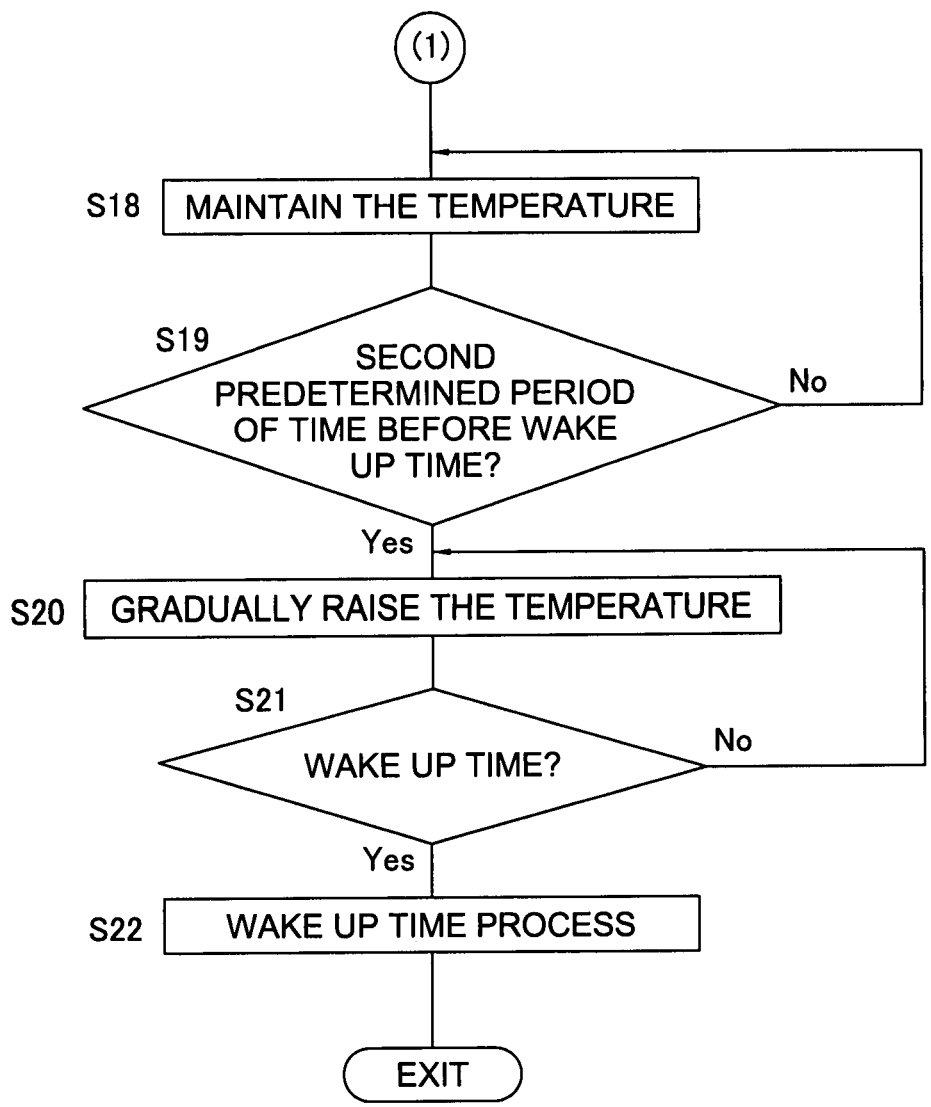
FIG. 5 is a flowchart showing the flow of the sleeping state improvement process.

The detail of sleeping state improvement process S6 shown in FIG. 3 is described by using the flowcharts shown in FIG. 4 and FIG. 5.

In step S10 shown in FIG. 4, the sleep duration is determined. In other words, the control unit 32 shown in FIG. 2 determines the sleep duration of the user P (see FIG. 1) based on the individual attribute information. Here, the individual attribute information is information regarding the age of the user P (see FIG. 1).

In step S11 shown in FIG. 4, whether or not the user P (see FIG. 1) falls asleep is detected. In other words, the transmitter 11 of the microwave Doppler sensor 10 shown in FIG. 2 transmits microwave to the user P (see FIG. 1). Note that microwave has characteristics to penetrate cloth, feather, artificial fiber, etc., which are materials of the bed 20 and clothing, and reflect off the body surface, the metal and the like. The receiver 12 receives a reflected wave. Here, the reflected wave is generated as a result of reflection of microwave from body surface of the user P (see FIG. 1). In other words, the microwave Doppler sensor 10 obtains the microwave and reflected wave without contacting the user P (see FIG. 1). The computing unit 14 receives a microwave signal from the transmitter 11 via the processing unit 13. The computing unit 14 receives a reflected wave signal from the receiver 12 via the processing unit 13. The computing unit 14 computes change information. The change information is information regarding the change in the reflected wave signal with respect to the microwave signal. The computing unit 14 converts the change information to information regarding the amount of body movement. The processing unit 13 receives information regarding the amount of body movement from the computing unit 14 and sends the same to the control device 30.

In step S12 shown in FIG. 4, whether or not the user P falls asleep is determined. In other words, the control unit 32 of the control device 30 shown in FIG. 2 receives information regarding the amount of body movement from the microwave Doppler sensor 10 of the bed 20. The control unit 32 determines whether or not the user P (see FIG. 1) falls asleep based on information regarding the amount of body movement. When it is determined that the user P (see FIG. 1) falls asleep, the process proceeds to step S13, and when it is determined that the user P (see FIG. 1) does not fall asleep, the process proceeds to step S11.

In step S13 shown in FIG. 4, sleep onset is detected. In other words, the transmitter 11 of the microwave Doppler sensor 10 shown in FIG. 2 transmits microwave to the user P (see FIG. 1). Note that microwave has characteristics to penetrate cloth, feather, artificial fiber, etc., which are materials of the bed 20 and clothing, and reflect off the body surface, the metal and the like. The receiver 12 receives a reflected wave. Here, the reflected wave is generated as a result of reflection of microwave from the body surface of the user P (see FIG. 1). In other words, the microwave Doppler sensor 10 obtains the microwave and reflected wave without contacting the user P (see FIG. 1). The computing unit 14 receives a microwave signal from the transmitter 11 via the processing unit 13. The computing unit 14 receives a reflected wave signal from the receiver 12 via the processing unit 13. The computing unit 14 computes change information. Change information is information regarding the change in the reflected wave signal with respect to the microwave signal. The computing unit 14 converts the change information to information regarding the amount of body movement. The processing unit 13 receives information regarding the amount of body movement from the computing unit 14 and sends the same to the control device 30.

In step S14 shown in FIG. 4, whether or not the user P has reached sleep onset is determined. In other words, the control unit 32 of the control device 30 shown in FIG. 2 receives information regarding the amount of body movement from the microwave Doppler sensor 10 of the bed 20. The control unit 32 determines whether or not the user P (see FIG. 1) has reached sleep onset based on information regarding the amount of body movement. When it is determined that the user P (see FIG. 1) has reached sleep onset, the process proceeds to step S15, and when it is determined that the user P (see FIG. 1) has not reached sleep onset, the process proceeds to step S13.

In step S15 shown in FIG. 4, the time of sleep onset is specified. In other words, the control unit 32 of the control device 30 shown in FIG. 2 refers to the timer (not shown) and specifies the time of sleep onset. The control unit 32 presumably determines the expected wake up time of the user P (see FIG. 1) based on information regarding the sleep duration and information regarding the time of sleep onset of the user P (see FIG. 1).

In step S16 shown in FIG. 4, control is performed such that the temperature is gradually lowered. In other words, the control unit 32 of the control device 30 shown in FIG. 2 generates a control signal to gradually lower a predetermined temperature and sends the same to the air conditioner 50. The air conditioner 50 receives from the control device 30 the control signal to gradually lower a predetermined temperature, and provides an air-conditioned environment around the user P (see FIG. 1) based on the control signal.

In step S17 shown in FIG. 4, whether or not the first predetermined period of time has elapsed is determined. In other words, the control unit 32 refers to the timer (not shown) and determines whether or not the first predetermined period of time has elapsed based on information regarding the time of sleep onset and information regarding the first predetermined period of time. When it is determined that the first predetermined period of time has elapsed, the process proceeds to step S18 ((1) shown in FIG. 4 and FIG. 5), and when it is determined that the first predetermined period of time has not elapsed, the process proceeds to step S16.

In step S18 ((1) shown in FIG. 5) shown in FIG. 5, the temperature is maintained. In other words, the control unit 32 of the control device 30 shown in FIG. 2 generates a control signal to maintain the temperature and sends the same to the air conditioner 50. The air conditioner 50 receives from the control device 30 the control signal to maintain the temperature, and provides an air-conditioned environment around the user P (see FIG. 1) based on the control signal.

In step S19 shown in FIG. 5, it is determined whether or not the second predetermined period of time before the expected wake up time has elapsed. In other words, the control unit 32 of the control device 30 shown in FIG. 2 refers to the timer (not shown) and determines whether or not the second predetermined period of time before the expected wake up time has elapsed based on information regarding the expected wake up time and information regarding the second predetermined period of time. When it is determined that the second predetermined period of time before the expected wake up time has elapsed, the process proceeds to step S20, and when it is determined that the second predetermined period of time before the expected wake up time has not elapsed, the process proceeds to step S18.

In step S20 shown in FIG. 5, control is performed such that the temperature is gradually raised. In other words, the control unit 32 of the control device 30 shown in FIG. 2 generates a control signal to gradually raise the maintained temperature and sends the same to the air conditioner 50. The air conditioner 50 receives from the control device 30 the control signal to gradually raise the maintained temperature, and provides an air-conditioned environment around the user P (see FIG. 1) based on the control signal.

In step S21 shown in FIG. 5, whether or not it is wake up time is determined. In other words, the control unit 32 of the control device 30 shown in FIG. 2 refers to the timer (not shown) and determines whether or not it is wake up time based on information regarding the expected wake up time. When it is determined that it is wake up time, the process proceeds to step S22, and when it is determined that it is not wake up time, the process proceeds to step S20.

In step S22 shown in FIG. 5, a wake up time process is performed. In other words, the control unit 32 of the control device 30 shown in FIG. 2 causes the buzzer (not shown) or the like to sound an alarm in order to wake up the user P (see FIG. 1).

<Characteristics of the Sleeping State Improvement System 1>

(1)

Here, the memory device 70 shown in FIG. 2 can be carried by the user P (see FIG. 1). The individual information is read out from the memory device 70. The specification unit 31 of the control device 30 shown in FIG. 2 receives the individual information from the control unit 32. The specification unit 31 specifies the individual attribute information of the user P (see FIG. 1) based on the individual information. Here, the individual information is the individual attribute information of the user P (see FIG. 1). The control unit 32 receives the individual attribute information from the specification unit 31. The control unit 32 controls the environment during sleep of the user P (see FIG. 1) based on the individual attribute information.

Therefore, since the individual attribute information of the user P (see FIG. 1) is specified based on the individual information, it is possible to specify the individual attribute information of the user P (see FIG. 1) even when the user P (see FIG. 1) sleeps away from home. In addition, since the environment during sleep of the user P (see FIG. 1) is controlled based on the individual attribute information, it is possible to control the environment during sleep according to individual difference of the user P (see FIG. 1). Consequently, it is possible to improve the sleeping state of the user P (see FIG. 1) even when the user sleeps away from home.

(2)

Here, the memory device 70 shown in FIG. 2 can be carried by the user P (see FIG. 1). The read-out device 40 reads out the individual information from the memory device 70. The specification unit 31 receives the individual information from the control unit 32. The specification unit 31 specifies the individual attribute information of the user P (see FIG. 1) based on the individual information. Here, the individual information is the individual attribute information of the user P (see FIG. 1). The control unit 32 receives the individual attribute information from the specification unit 31. The control unit 32 controls the environment during sleep of the user P (see FIG. 1) based on the individual attribute information.

Therefore, since the individual attribute information of the user P (see FIG. 1) is specified based on the individual information, it is possible to specify the individual attribute information of the user P (see FIG. 1) even when the user P (see FIG. 1) sleeps away from home. In addition, since the environment during sleep of the user P (see FIG. 1) is controlled based on the individual attribute information, it is possible to control the environment during sleep according to individual difference of the user P (see FIG. 1). Consequently, it is possible to improve the sleeping state of the user P (see FIG. 1) even when the user P (see FIG. 1) sleeps away from home.

(3)

Here, the memory device 70 shown in FIG. 2 can be carried by the user P (see FIG. 1). The individual information is read from the memory device 70. The individual information includes the individual attribute information of the user P (see FIG. 1). The specification unit 31 receives the individual information from the control unit 32. The specification unit 31 specifies the individual attribute information of the user P (see FIG. 1) based on the individual information. Here, the individual information is the individual attribute information of the user P (see FIG. 1). The control unit 32 receives the individual attribute information from the specification unit 31. The control unit 32 controls the environment during sleep of the user P (see FIG. 1) based on the individual attribute information.

Therefore, since the individual information is the individual attribute information of the user P (see FIG. 1), it is possible to read out the individual attribute information from the memory device 70 and control the environment during sleep of the user P (see FIG. 1) based on the individual attribute information.

(4)

Here, the memory device 70 shown in FIG. 2 can be carried by the user P (see FIG. 1). The individual attribute information is input to the input unit 62 of the write-in device 60. The individual attribute information is stored in the memory device 70. The individual information is read from the memory device 70. The specification unit 31 receives the individual information from the control unit 32. The specification unit 31 receives the individual attribute information from the control unit 32. The specification unit 31 specifies the individual attribute information of the user P (see FIG. 1) based on the individual information. Here, the individual information is the individual attribute information of the user P (see FIG. 1). The control unit 32 receives the individual attribute information from the specification unit 31. The control unit 32 controls the environment during sleep of the user P (see FIG. 1) based on the individual attribute information.

Therefore, since the individual attribute information is input, it is possible to store the individual attribute information of the user P (see FIG. 1) and specify the individual attribute information of the user P (see FIG. 1) based on the individual information.

(5)

Here, the memory device 70 shown in FIG. 2 can be carried by the user P (see FIG. 1). The individual attribute information is input to the input unit 62 of the write-in device 60. The individual attribute information is information regarding the age of the user P (see FIG. 1). The individual attribute information is stored in the memory device 70. The individual information is read from the memory device 70. The specification unit 31 receives the individual information from the control unit 32. The specification unit 31 receives the individual information from the control unit 32. The specification unit 31 specifies the individual attribute information of the user P (see FIG. 1) based on the individual information. Here, the individual information is the individual attribute information of the user P (see FIG. 1). The control unit 32 receives the individual attribute information from the specification unit 31. The control unit 32 controls the environment during sleep of the user P (see FIG. 1) based on the individual attribute information.

Therefore, since the individual attribute information can be used as static information, it is possible to control the environment during sleep according to the static information of the user P (see FIG. 1).

(6)

Here, the memory device 70 shown in FIG. 2 can be carried by the user P (see FIG. 1). The individual information is read from the memory device 70. The specification unit 31 receives the individual information from the control unit 32. The specification unit 31 specifies the individual attribute information of the user P (see FIG. 1) based on the individual information. Here, the individual information is the individual attribute information of the user P (see FIG. 1). The control unit 32 receives the individual attribute information from the specification unit 31. The microwave Doppler sensor 10 detects sleep onset of the user P (see FIG. 1) based on the biological information. Here, the biological information is information regarding body movement of the user P (see FIG. 1). The control unit 32 receives information regarding sleep onset of the user P (see FIG. 1) from the microwave Doppler sensor 10. The control unit 32 controls the environment during sleep of the user based on the individual attribute information.

Therefore, since sleep onset of the user P (see FIG. 1) is detected based on the biological information, it is possible to determine the timing to start controlling the environment during sleep of user P (see FIG. 1).

(7)

Here, the microwave Doppler sensor 10 shown in FIG. 2 detects sleep onset of the user P (see FIG. 1) based on the biological information. The control unit 32 receives information regarding sleep onset of the user P (see FIG. 1) from the microwave Doppler sensor 10. The control unit 32 gradually lowers the temperature over the first predetermined period of time from sleep onset of the user P (see FIG. 1), and gradually raises the temperature over the second predetermined period of time until sleep offset of the user P (see FIG. 1).

Therefore, the control unit 32 gradually lowers the temperature over the first predetermined period of time from sleep onset of the user P (see FIG. 1), and gradually raises the temperature over the second predetermined period of time until sleep offset of the user P (see FIG. 1), it is possible to control the temperature during sleep of user P (see FIG. 1) so that the temperature fits the biological rhythm of the user P (see FIG. 1).

(8)

Here, the memory device 70 shown in FIG. 2 can be carried by the user P (see FIG. 1). The individual information is read from the memory device 70. The specification unit 31 receives the individual information from the control unit 32. The specification unit 31 specifies the individual attribute information of the user P (see FIG. 1) based on the individual information. Here, the individual information is the individual attribute information of the user P (see FIG. 1). The control unit 32 receives the individual attribute information from the specification unit 31. The control unit 32 controls the environment during sleep of the user P (see FIG. 1) based on the individual attribute information. The control unit 32 controls the environment during sleep of the user P (see FIG. 1) by controlling the air conditioner 50. The environment refers to an air-conditioned environment. The air-conditioned environment refers to the temperature of air-conditioned air blown out from the air conditioner 50.

Therefore, since the air-conditioned environment during sleep of the user P (see FIG. 1) is controlled based on the individual attribute information, it is possible to control the air-conditioned environment during sleep according to individual difference of the user P (see FIG. 1).

Alternative Embodiment of the First Embodiment (A) The bed 20 shown in FIG. 2 may not need to comprise the microwave Doppler sensor 10. At this time, the control unit 32 of the control device 30 may presumably determine that the user P (see FIG. 1) has reached sleep onset based on that the read-out device 40 read out the individual information from the memory device 70. In other words, it may be presumably determined that the user P (see FIG. 1) has reached sleep onset when the control unit 32 of the control device 30 received the individual information from the memory unit 41 of the read-out device 40.

Therefore, since it is presumably determined that the user P (see FIG. 1) has reached sleep onset based on that the read-out device 40 read out the individual information, it is possible to control the environment during sleep of the user P (see FIG. 1) even when the user P (see FIG. 1) sleeps away from home and sleep onset cannot be detected.

(B) The individual attribute information may include at least one of the following: age, sex, degree of obesity, physical condition, and race of the user. When a plurality of pieces of information is used as the individual attribute information, it is possible to minutely control the environment during sleep of the user P (see FIG. 1).

In addition, the individual information may include information other than the individual attribute information. For example, it may include identification information, which is information to identify the user P (see FIG. 1). The identification information may, for example, be the name of the user P (see FIG. 1), an identification number assigned to the user P (see FIG. 1), and the like. In this case, in step S5 shown in FIG. 3, the specification unit 31 extracts the individual attribute information from the individual information (identification information, individual attribute information).

(C) An air-conditioned environment controlled by the control unit 32 of the control device 30 shown in FIG. 2 may refer to at least one of the following: temperature of air-conditioned air blown out from the air conditioner 50, humidity of air-conditioned air blown out from the air conditioner 50, flow direction of air-conditioned air blown out from the air conditioner 50, volume of air-conditioned air blown out from the air conditioner 50, cleanliness of air-conditioned air blown out from the air conditioner 50, and amount of ventilation provided by the air conditioner 50. When the control unit 32 controls a plurality of air-conditioned environments, it is possible to minutely control the environment during sleep of the user P (see FIG. 1).

For example, an air-conditioned environment may be controlled such that the temperature of the area around the head of the user P (see FIG. 1) is lower and the temperature of the area around the feet of the user P (see FIG. 1) is higher (for example, the temperature difference between the head area and feet area is 4 degree C.), before sleep onset of the user P (see FIG. 1) is detected in step S13 shown in FIG. 4. In this case, it is possible to hold the user P (see FIG. 1) in a condition where "head is cool and feet are warm," thus sleep onset of the user P (see FIG. 1) can be facilitated.

(D) The control unit 32 of the control device 30 shown in FIG. 2 may control at least one of the following: air-conditioned environment, lighting environment, acoustic environment, and odor environment. For example, in step S22 shown in FIG. 5, it may be possible to cause a lighting system (not shown) instead of the buzzer (not shown) to inform (such as by lighting up) and wake up the user P (see FIG. 1). In this case, it is possible to wake up the user P (see FIG. 1) in a more natural way. For example, in step S18 shown in FIG. 5, it may be possible to cause a fragrance device (not shown) to release fragrance that helps relaxing the automatic nerve system of the user P (see FIG. 1). In this case, it is possible to further improve the sleeping state of the user P (see FIG. 1).

(E) The memory device 70 shown in FIG. 1 may be any type of member as long as it can be carried by the user P (see FIG. 1) and store the individual information. For example, it may be a memory card, an IC tag, or a personal digital assistant such as a cellular phone. The memory device 70 may be a non-contact type or a contact type. When the memory device 70 is a contact type, the read-out device 40 and the write-in device 60 deliver information via a wired network instead of the wireless network. The bed 20 may be a seat in a vehicle, such as airplane. In this case, the air conditioner 50 may be a personal air conditioner exclusively used by the user P (see FIG. 1).

Figure 6:
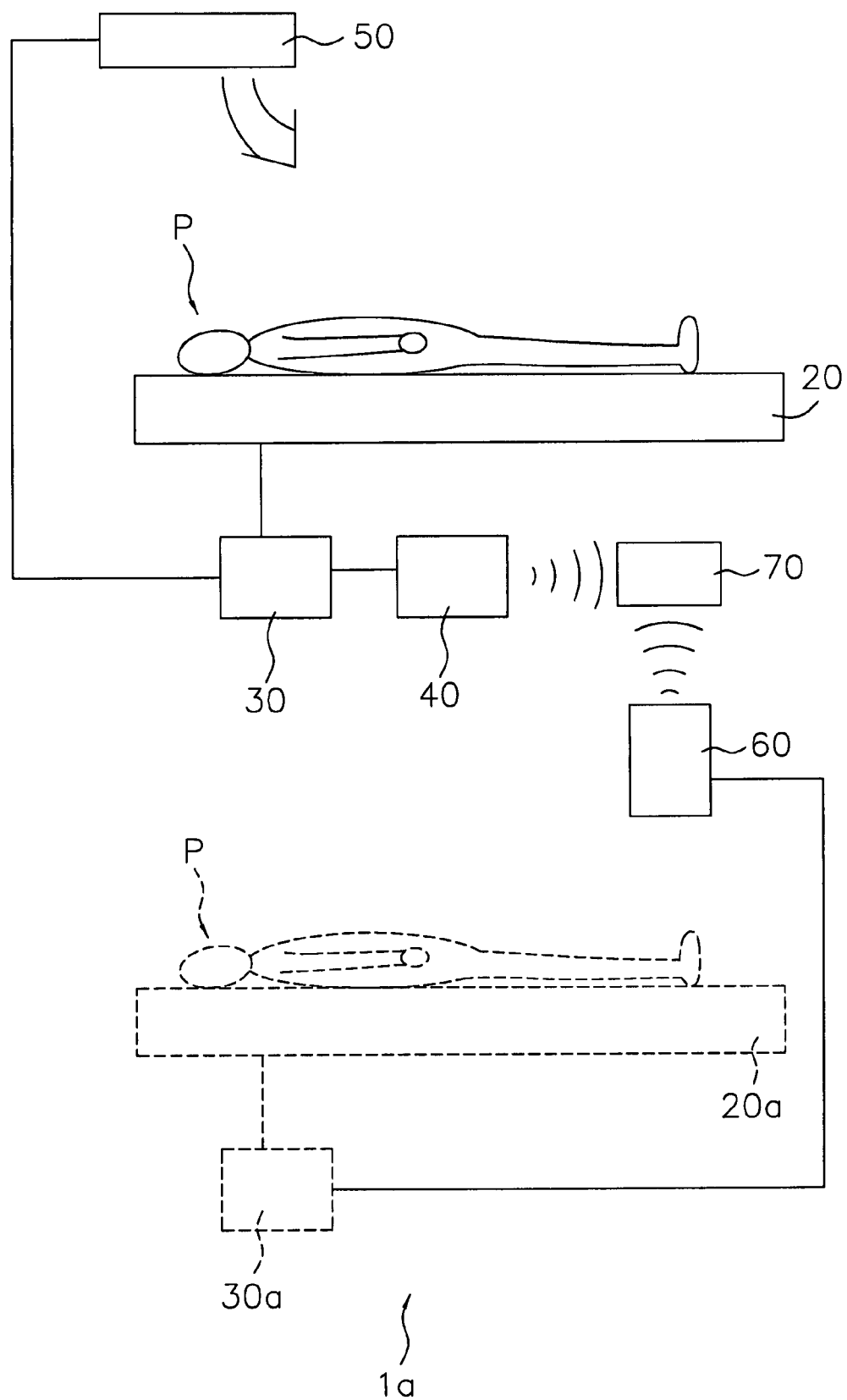
FIG. 6 is a schematic diagram of the sleeping state improvement system according to the first embodiment of the present invention (alternative embodiment).
Figure 7:
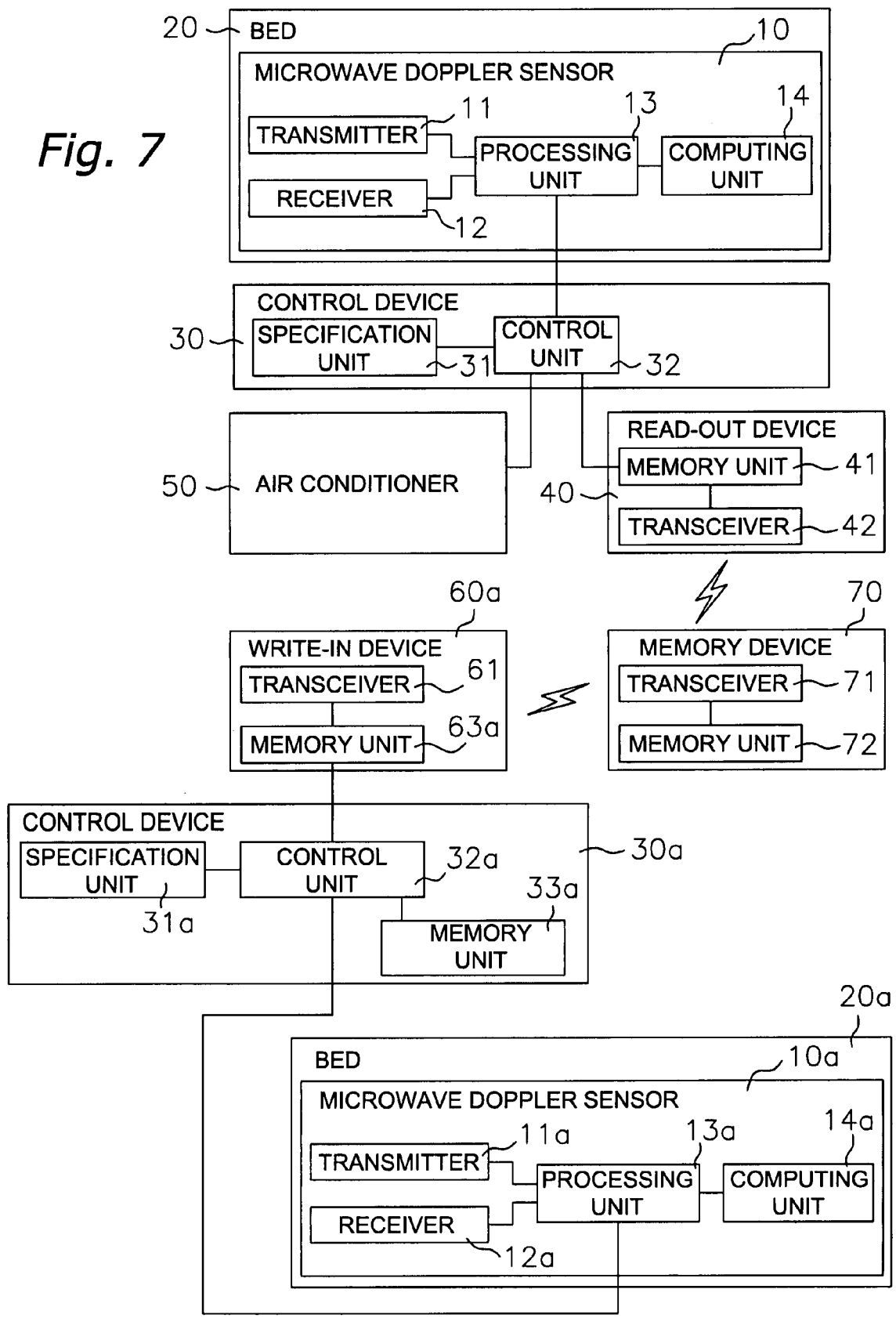
FIG. 7 is a block diagram of the sleeping state improvement system according to the first embodiment of the present invention (alternative embodiment).

(F) As shown in FIG. 6, a sleeping state improvement system 1a may further comprise a bed 20a and a control device 30a. The bed 20a and the control device 30a are provided in a place where the user P (see FIG. 6) usually sleeps such as the house of the user P (see FIG. 6). As shown in FIG. 7, the bed 20a shown in FIG. 6 mainly comprises a microwave Doppler sensor 10a. The microwave Doppler sensor 10a mainly comprises a transmitter 11a, a receiver 12a, a processing unit 13a, and a computing unit 14a. The control device 30a mainly comprises a specification unit 31a, a control unit 32a, and a memory unit 33a. In addition, the write-in device 60a does not comprise the input unit 62 but comprises a memory unit 63a.

The microwave Doppler sensor 10a detects biological information. Here, the biological information is information regarding body movement of the user P (see FIG. 6). The control unit 32a of the control device 30a receives information regarding the amount of body movement from the microwave Doppler sensor 10a, and determines sleep onset based on information regarding the amount of body movement. The control unit 32a refers to a timer (not shown) and specifies the time of sleep onset when determined that the user P (see FIG. 6) has reached sleep onset. The control unit 32a receives information regarding the amount of body movement from the microwave Doppler sensor 10a and determines whether or not the user P (see FIG. 6) is awake based on information regarding the amount of body movement. The control unit 32a refers to the timer (not shown) and specifies the wake up time when determined that the user P (see FIG. 6) has reached sleep offset. The control unit 32a computes the sleep duration based on information regarding the time of sleep onset and information regarding the wake up time. The control unit 32a causes the memory unit 33a to store information regarding the sleep duration. The control unit 32a refers to the memory unit 33a and computes the average sleep duration of the user P (see FIG. 6) based on information regarding the sleep duration. In other words, the microwave Doppler sensor 10a detects sleep onset of the user P (see FIG. 6) and sleep offset of the user P (see FIG. 6) based on the biological information, and thereby detects the individual attribute information (average sleep duration of the user P (see FIG. 6)). The control unit 32a sends the individual attribute information to the write-in device 60a.

The memory unit 63a of the write-in device 60a receives the individual attribute information from the control device 30a and stores the same. The transceiver 61 receives the individual attribute information from the memory unit 63a and transmits the same to the memory device 70 via the wireless network. This alternative embodiment is different from the first embodiment in these points.

Figure 8:
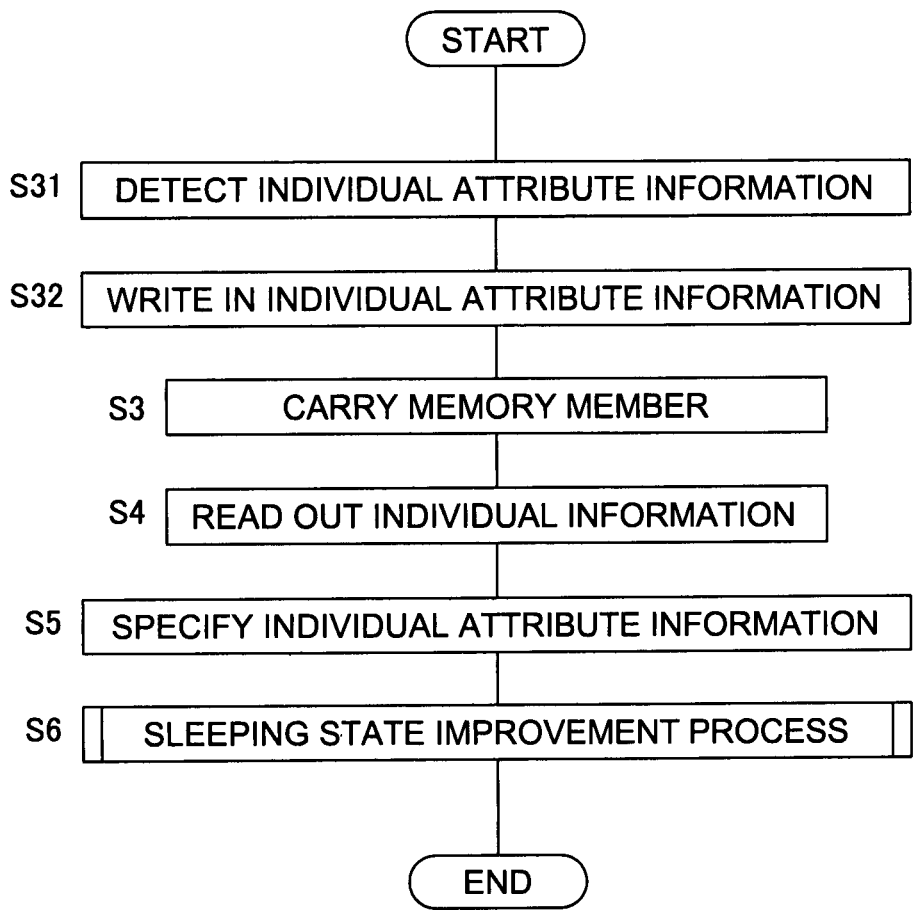
FIG. 8 is a flowchart showing a flow of a process in which the sleeping state improvement system improves a user's sleeping state (alternative embodiment).

In this case, as shown in FIG. 8, a flow of the process in which the sleeping state improvement system 1a improves the sleeping state of the user P (see FIG. 6) is different from the first embodiment in the following points. In FIG. 8, the same process as in the first embodiment is indicated with the same symbols and the description thereof is omitted.

In step S31 shown in FIG. 8, the individual attribute information is detected. In other words, the microwave Doppler sensor 10a of the bed 20a shown in FIG. 6 detects biological information. Here, biological information is information regarding body movement of the user P (see FIG. 6). The control unit 32a of the control device 30a receives information regarding the amount of body movement from the microwave Doppler sensor 10a and determines sleep onset based on information regarding the amount of body movement. The control unit 32a refers to the timer (not shown) and specifies the time of sleep onset when determined that the user P (see FIG. 6) has reached sleep onset. The control unit 32a receives information regarding the amount of body movement from the microwave Doppler sensor 10a and determines whether or not the user P (see FIG. 6) is awake based on information regarding the amount of body movement. The control unit 32a refers to the timer (not shown) and specifies the wake up time when determined that the user P (see FIG. 6) has reached sleep offset. The control unit 32a computes the sleep duration based on information regarding the time of sleep onset and information regarding the wake up time. The control unit 32a causes the memory unit 33a to store information regarding the sleep duration. The control unit 32a refers to the memory unit 33a and computes the average sleep duration of the user P (see FIG. 6) based on information regarding the sleep duration. In other words, the microwave Doppler sensor 10a detects sleep onset of the user P (see FIG. 6) and sleep offset of the user P (see FIG. 6) based on the biological information, and thereby detects the individual attribute information (average sleep duration of the user P (see FIG. 6)). The control unit 32a sends the individual attribute information to the write-in device 60a. The memory unit 63a of the write-in device 60a receives the individual attribute information from the control device 30a and stores the same.

In step S32 shown in FIG. 8, the individual attribute information is written. In other words, the transceiver 61 of the write-in device 60a shown in FIG. 7 receives the individual attribute information from the memory unit 63a and sends the same to the memory device 70 via the wireless network. The transceiver 71 of the memory device 70 receives the individual attribute information from the write-in device 60a via the wireless network. The memory unit 72 receives the individual attribute information from the transceiver 71 and stores the same. In other words, the individual attribute information is written into the memory device 70.

Therefore, since sleep onset of the user P (see FIG. 6) is detected based on the biological information, it is possible to determine the timing to start controlling the environment during sleep of user P (see FIG. 6). In addition, since the individual attribute information is detected, it is possible to store the individual attribute information of the user P (see FIG. 6) and specify the individual attribute information of the user P (see FIG. 6) based on the individual information. Further, since the individual attribute information includes the average sleep duration of the user P (see FIG. 6), it is possible to control the environment during sleep according to individual difference of the average sleep duration of the user P (see FIG. 6). In addition, since the individual attribute information can be used as dynamic information, it is possible to control the environment during sleep according to the dynamic information of the user P (see FIG. 6).

(G) In the above described alternative embodiment (F), biological information may be information regarding at least one of the following: body movement, heartbeat, and breathing of the user P (see FIG. 6).

When biological information is information regarding the heartbeat of the user P (see FIG. 6), the microwave Doppler sensor 10a shown in FIG. 6 is not provided to the bed 20a, but provided to a place such as the ceiling above the chest the user P (see FIG. 6), where the microwave Doppler sensor 10a can transmit microwave to the chest of the user P (see FIG. 6). At this time, the microwave Doppler sensor 10a may further comprise an amplifier (not shown), an extraction unit (not shown), and an analyzer (not shown). In this case, the amplifier (not shown) receives a microwave signal from the transmitter 11a. The amplifier (not shown) receives a reflected wave signal from the receiver 12a. The amplifier (not shown) amplifies the microwave signal and the reflected wave signal. The computing unit 14a receives a signal regarding microwave from the amplifier (not shown) via the processing unit 13a. Here, the signal regarding microwave is a signal generated as a result of amplification of the microwave signal. The computing unit 14a receives a signal regarding reflected wave from the amplifier (not shown) via the processing unit 13a. Here, the signal regarding reflected wave is a signal generated as a result of amplification of the reflected wave signal. The computing unit 14a computes change information. Here, the change information is information regarding the change in the signal regarding reflected wave with respect to the signal regarding microwave. The extraction unit (not shown) receives change information from the computing unit 14a via the processing unit 13a. The extraction unit (not shown) extracts band information based on the change information. The band information is information regarding a predetermined frequency bandwidth (frequency bandwidth corresponding to the frequency of the heartbeat). The analyzer (not shown) receives the band information from the extraction unit (not shown) via the processing unit 13a. The analyzer (not shown) analyzes subtle body movement generated by the heartbeat of the user P (see FIG. 6) based on the band information. Consequently, the analyzer (not shown) analyses the heartbeat information based on the band information. Here, the heartbeat information is information regarding, for example, the stress level. Note that the microwave Doppler sensor 10 is the same as the microwave Doppler sensor 10a.

When the biological information is information regarding the breathing of the user P (see FIG. 6), as in the case described above, information regarding the breathing of the user P (see FIG. 6) may be detected based on the heartbeat information, and information regarding the breathing of the user P (see FIG. 6) may be detected based on information (such as image information) on the movement of the lips of the user P (see FIG. 6).

In addition, the bed 20, 20a may comprise a mat type sensor instead of the microwave Doppler sensor 10, 10a. Also in this case, it is possible to detect the biological information.

(H) In the above described alternative embodiments (F), (G), the individual attribute information may include at least one of the following: average sleep duration of the user P (see FIG. 6) and the sleep duration of the user P (see FIG. 6) during a previous predetermined period of time. Therefore, since the individual attribute information includes the average sleep duration of the user P (see FIG. 6) and the like, it is possible to control the environment during sleep according to individual difference such as the average sleep duration of the user P (see FIG. 6) and the like.

For example, when the individual attribute information is the sleep duration in three days in the past, even when the user P (see FIG. 6) stayed up all night during the past three days, it is possible to adequately determine the sleep duration in step S10 shown in FIG. 4.

Second Embodiment

Figure 9:
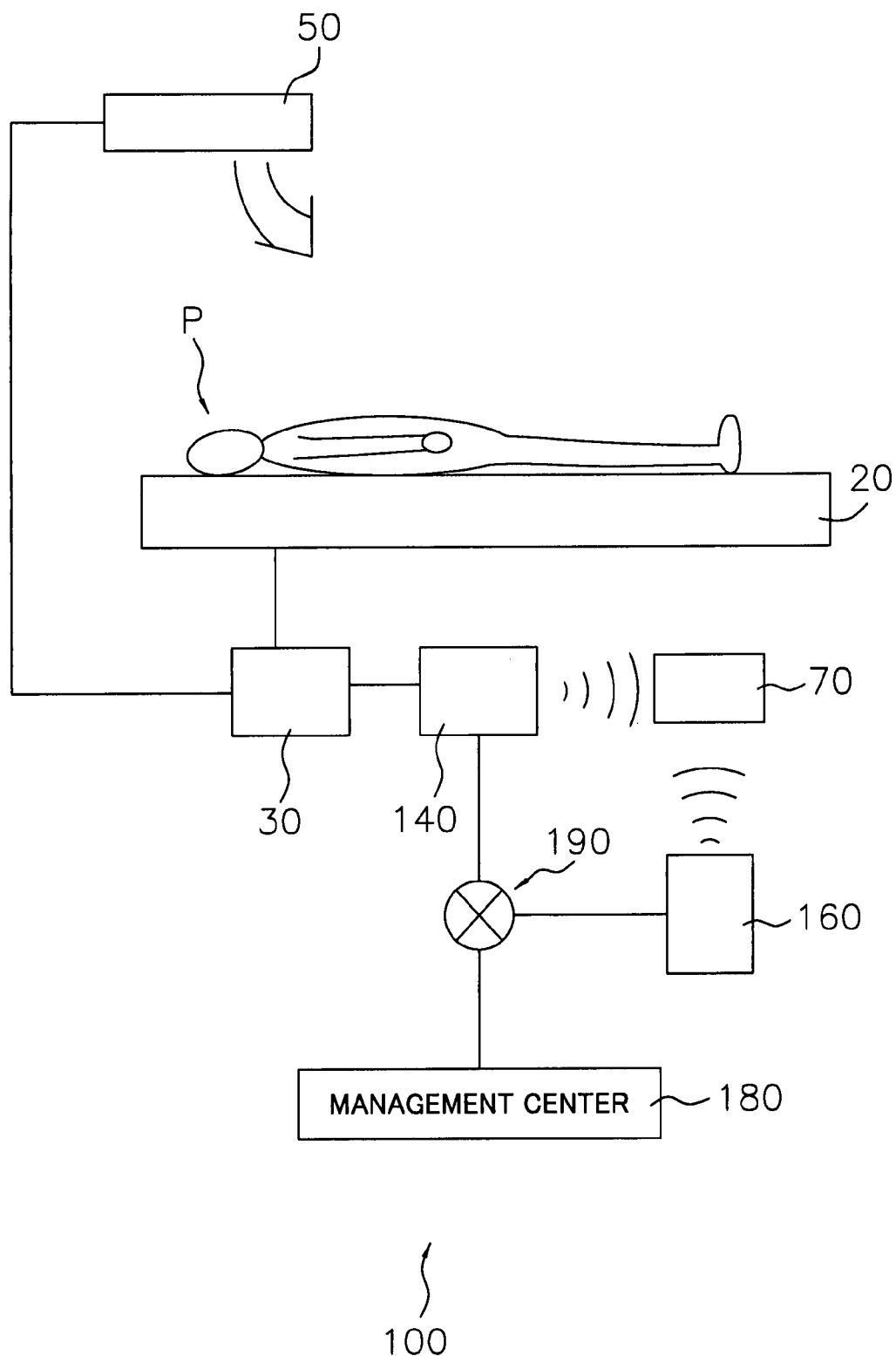
FIG. 9 is a schematic diagram of a sleeping state improvement system according to a second embodiment of the present invention.
Figure 10:
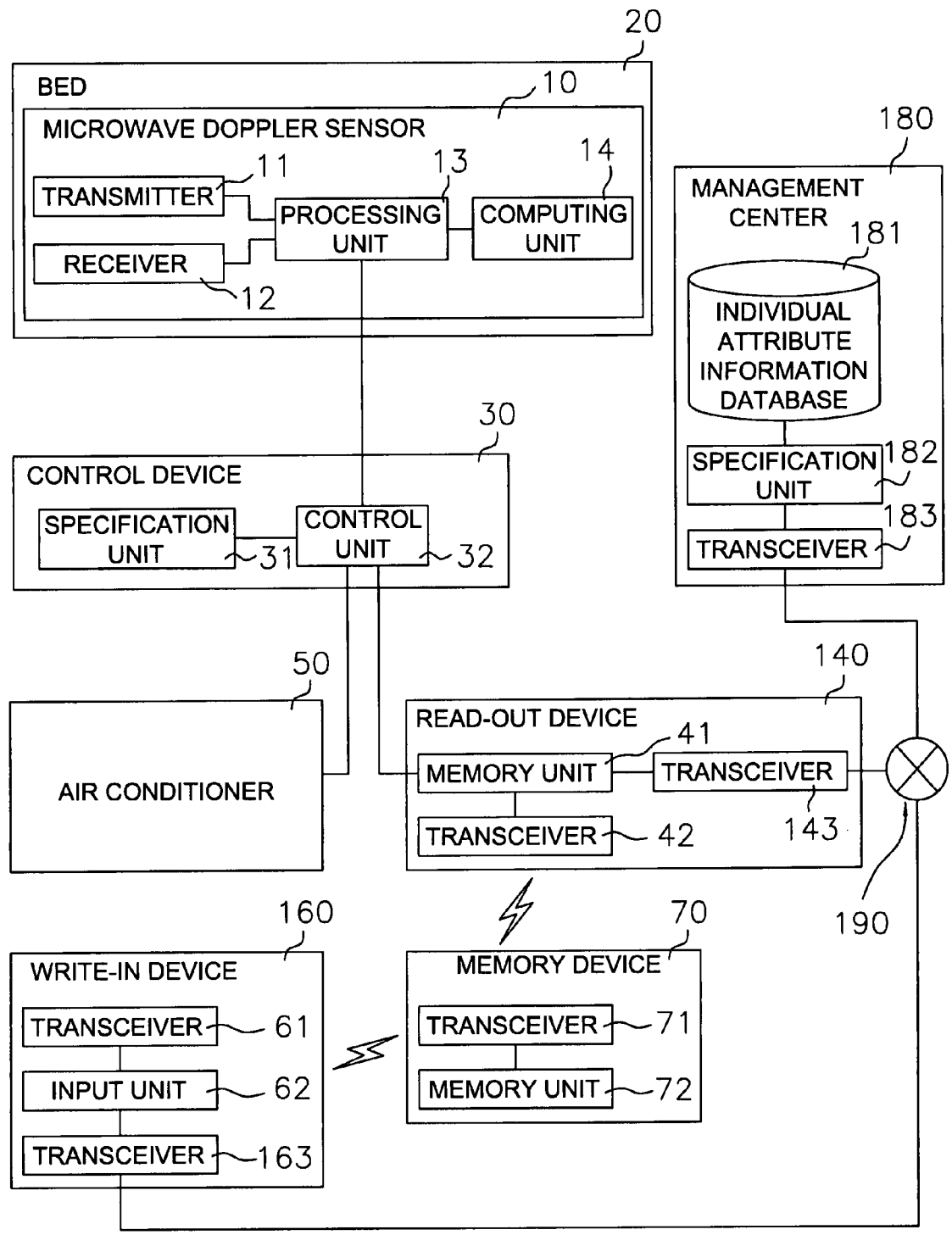
FIG. 10 is a block diagram of the sleeping state improvement system according to the second embodiment of the present invention.

FIG. 9 is a schematic diagram of the sleeping state improvement system 100 according to a second embodiment of the present invention. In addition, FIG. 10 is a block diagram of each component of the sleeping state improvement system 100 according to the second embodiment of the present invention. In FIG. 9 and FIG. 10, components same as the components of the sleeping state improvement system 1 shown in FIG. 1 and FIG. 2 are indicated by the same number. The sleeping state improvement system 100 shown in FIG. 9 is a system configured to primarily improve the sleeping state of a user P.

As shown in FIG. 9 and FIG. 10, the fundamental structure of this sleeping state improvement system 100 is the same as the first embodiment, and each component is the same as that shown in FIG. 2, however, it is different from the first embodiment in that the sleeping state improvement system 100 further comprises a management center 180 shown in FIG. 9. In other words, the management center 180, a read-out device 140, and a write-in device 160 are mutually connected via a network 190. As shown in FIG. 10, the management center 180 mainly comprises an individual attribute information database 181, a specification unit 182, and a transceiver 183. The write-in device 160 further comprises a transceiver 163. The read-out device 140 further comprises a transceiver 143.

Identification information and individual attribute information are input to the input unit 62 of the write-in device 160 shown in FIG. 10. Here, identification information is information to identify the user P (see FIG. 9). The individual attribute information is information regarding the age of the user P (see FIG. 1). The transceiver 61 receives the identification information from the input unit 62 and transmits the same to the memory device 70 via a wireless network. The transceiver 71 receives identification information from the write-in device 160 via the wireless network. The memory unit 72 receives the identification information from the transceiver 71 and stores the same. In other words, identification information is written into the memory device 70.

The transceiver 163 of the write-in device 160 receives the identification information and the individual attribute information from the input unit 62, and transmits the same to the management center 180 via the network 190. The transceiver 183 of the management center 180 receives the identification information and the individual attribute information from the write-in device 160 via the network 190. The individual attribute information database 181 receives the identification information and the individual attribute information from the transceiver 183 via the specification unit 182, and stores the individual attribute information for each user P (see FIG. 9). In other words, the individual attribute information database 181 stores the identification information and the individual attribute information in a corresponding manner.

The transceiver 42 of the read-out device 140 receives the individual information from the memory device 70 via the wireless network. Here, the individual information is the identification information.

The transceiver 143 of the read-out device 140 receives the identification information from the memory unit 41, and sends the identification information to the management center 180 via the network 190. The transceiver 183 of the management center 180 receives the identification information from the read-out device 140 via the network 190. The specification unit 182 receives the identification information from the transceiver 183. The specification unit 182 refers to the individual attribute information database 181 and specifies the individual attribute information of the user P (see FIG. 9) based on the identification information. The transceiver 183 receives the individual attribute information of the user P (see FIG. 9) from the specification unit 182 and sends the same to the read-out device 140 via the network 190. The transceiver 143 of the read-out device 140 receives the individual attribute information of the user P (see FIG. 9) from the management center 180 via the network 190. The memory unit 41 receives the individual attribute information of the user P (see FIG. 9) from the transceiver 143 and temporarily stores the same. This alternative embodiment is different from the first embodiment in these points.

Figure 11:
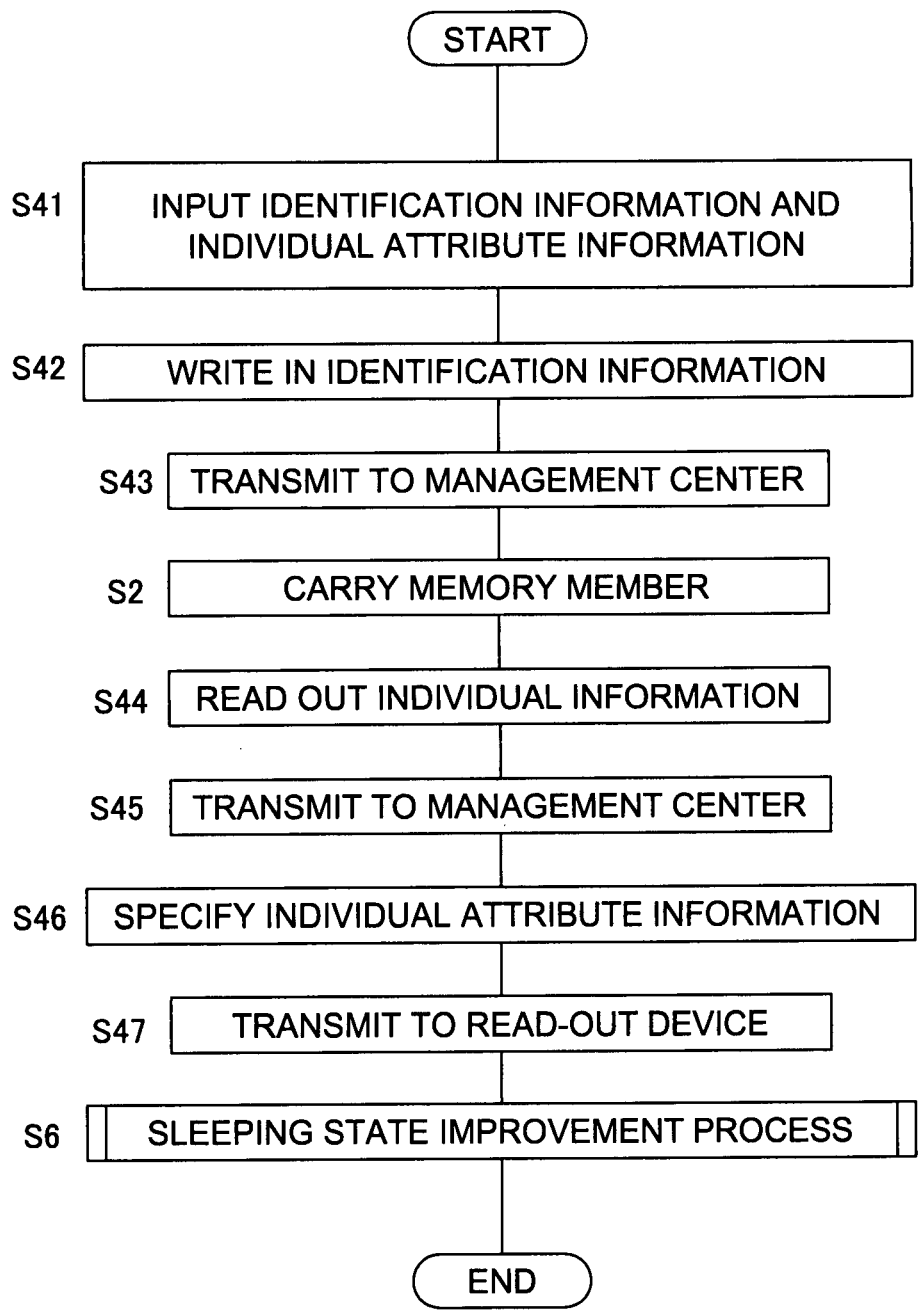
FIG. 11 is a flowchart showing a flow of a process in which the sleeping state improvement system improves a user's sleeping state.

In addition, as shown in FIG. 11, a flow of the process in which the sleeping state improvement system 100 improves the sleeping state of the user P (see FIG. 9) is different from the first embodiment in the following points. In FIG. 11, the same process as in the first embodiment is indicated with the same symbols and the description thereof is omitted.

In step S41 shown in FIG. 11, the identification information and the individual attribute information are input. In other words, the identification information and the individual attribute information are input to the input unit 62 of the write-in device 160 shown in FIG. 10. Here, identification information is information to identify the user P (see FIG. 9). The individual attribute information is information regarding the age of the user P (see FIG. 1).

In step S42 shown in FIG. 11, the identification information is written. In other words, the transceiver 61 of the write-in device 160 shown in FIG. 10 receives the identification information from the input unit 62 and sends the same to the memory device 70 via the wireless network. The transceiver 71 receives the identification information from the write-in device 160 via the wireless network. The memory unit 72 receives the identification information from the transceiver 71 and stores the same. In other words, the identification information is written into the memory device 70.

In step S43 shown in FIG. 11, the identification information and the individual attribute information are sent to the management center. In other words, the transceiver 163 of the write-in device 160 shown in FIG. 10 receives the identification information and the individual attribute information from the input unit 62, and transmits the same to the management center 180 via the network 190. The transceiver 183 of the management center 180 receives the identification information and the individual attribute information from the write-in device 160 via the network 190. The individual attribute information database 181 receives the identification information and the individual attribute information from the transceiver 183 via the specification unit 182, and stores the individual attribute information for each user P (see FIG. 9). In other words, the individual attribute information database 181 stores the identification information and the individual attribute information in a corresponding manner.

In step S44 shown in FIG. 11, the individual information is read out. In other words, the transceiver 42 of the read-out device 140 shown in FIG. 10 sends the memory member 70 via the wireless network a signal requiring reading out of the individual information. Here, the individual information is identification information. The transceiver 71 of the memory device 70 receives from the read-out device 140 via the wireless network a signal requiring reading out of the individual information, receives the individual information (identification information) from the memory unit 72 and sends the same to the read-out device 140 via the wireless network. The transceiver 42 of the read-out device 140 receives the individual information (identification information) from the memory device 70 via the wireless network. In other words, the individual information (identification information) is read out from the memory device 70. The memory unit 41 receives the individual information (identification information) from the transceiver 42 and temporarily stores the same.

In step S45 shown in FIG. 11, the identification information is sent to the management center. In other words, the transceiver 143 of the read-out device 140 shown in FIG. 10 receives the identification information from the memory unit 41 and sends the identification information to the management center 180 via the network 190. The transceiver 183 of the management center 180 receives the identification information from the read-out device 140 via the network 190.

In step S46 shown in FIG. 11, the individual attribute information is specified. In other words, the specification unit 182 of the management center 180 shown in FIG. 10 receives the identification information from the transceiver 183. The specification unit 182 refers to the individual attribute information database 181 and specifies the individual attribute information of the user P (see FIG. 9) based on the identification information.

In step S47 shown in FIG. 11, the individual attribute information is sent to the read-out device 140. In other words, the transceiver 183 of the management center 180 shown in FIG. 10 receives the individual attribute information of the user P (see FIG. 9) from the specification unit 182 and sends the same to the read-out device 140 via the network 190. The transceiver 143 of the read-out device 140 receives the individual attribute information of the user P (see FIG. 9) from the management center 180 via the network 190. The memory unit 41 receives the individual attribute information of the user P (see FIG. 9) from the transceiver 143 and temporarily stores the same. The control unit 32 of the control device 30 receives the individual attribute information from the memory unit 41.

Therefore, since the individual attribute information is stored in the management center 180, it is possible to save the memory capacity in the memory device 70. In addition, since the individual attribute information is stored in the management center 180, it is possible to lower the burden of the user P (see FIG. 9) to manage the individual attribute information. This alternative embodiment is different from the first embodiment in these points.

This alternative embodiment is the same as the first embodiment in that the individual attribute information of the user P (see FIG. 9) is specified based on the individual information, and thus it is possible to specify the individual attribute information of the user P (see FIG. 9) even when the user P (see FIG. 9) sleeps away from home. In addition, this embodiment is the same as the first embodiment in that the environment during sleep of the user P (see FIG. 9) is controlled based on the individual attribute information and thus it is possible to control the environment during sleep according to individual difference of the user P (see FIG. 9). Therefore, also with this type of the sleeping state improvement system 100, it is possible to improve the sleeping state of the user P (see FIG. 9) even when the user sleeps away from home.

Alternative of the Second Embodiment (A) The bed 20 shown in FIG. 10 may not need to comprise the microwave Doppler sensor 10. At this time, the control unit 32 of the control device 30 may presumably determine that the user P (see FIG. 1) has reached sleep onset based on that the read-out device 140 received the individual attribute information via the network 190. In other words, it may be presumably determined that the user P (see FIG. 1) has reached sleep onset when the control unit 32 of the control device 30 receives the individual attribute information from the memory unit 41 of the read-out device 40.

Therefore, since it is presumably determined that the user P (see FIG. 9) has reached sleep onset based on that the read-out device 40 received the individual attribute information via the network 190, it is possible to control the environment during sleep of the user P (see FIG. 9) even when the user P (see FIG. 9) sleeps away from home and sleep onset cannot be detected.

Figure 12:
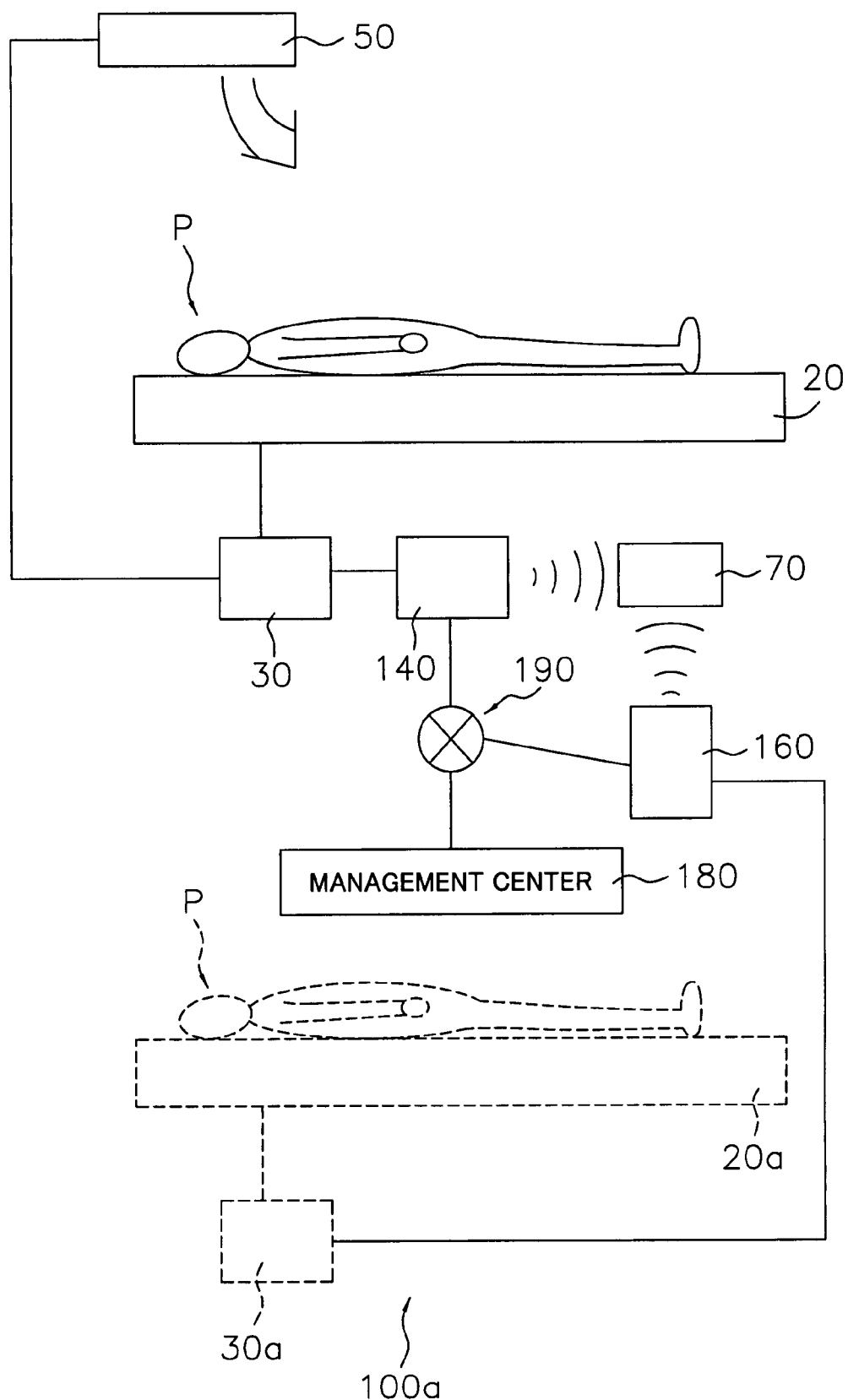
FIG. 12 is a schematic diagram of the sleeping state improvement system according to the second embodiment of the present invention (alternative embodiment).

(B) As shown in FIG. 12, as is the case with the alternative embodiment (F) in the first embodiment, the sleeping state improvement system 100a may further comprise the bed 20a and the control device 30a.

(C) The control device 30 shown in FIG. 10 may not need to comprise the specification unit 31.

INDUSTRIAL APPLICABILITY

The sleeping state improvement system and the sleeping state improvement method according to the present invention have effects of improving the sleeping state of the user even when the user sleeps away from home, and are useful as the sleeping state improvement system and the sleeping state improvement method, etc.

What is claimed is:
1. A sleeping state improvement system configured to improve a sleeping state of a user, comprising:
    a memory device that can be carried by the user from a first place to a second place, the second place being different from the first place, and the first and second places being places where the user sleeps with the first place being a place where the user usually sleeps;
    a first detection unit configured to detect biological information of the user and further detect individual attribute information of the user based on the biological information of the user during sleep of the user in the first place, the first detection unit being located in the first place;
    a first write-in device configured to write-in the individual attribute information detected by the first detection unit to the memory device in the first place;
    a read-out device configured to read out the individual attribute information from the memory device carried to the second place by the user, the read-out device being located in the second place; and
    a control unit configured to control an environment in the second place during sleep of the user in the second place based on the individual attribute information read out by the read-out device from the memory device carried to the second place by the user, the control unit being located in the second place,
    the memory device being configured to communicate with the first write-in device and the read-out device, the memory device being carryable from the first place to the second place without carrying the first detection unit and the first write-in device from the first place to the second place.

2. The sleeping state improvement system according to claim 1, wherein
    the individual attribute information includes at least one of the following: age, sex, degree of obesity, physical condition, and race of the user.

3. The sleeping state improvement system according to claim 1, wherein
    the biological information includes information regarding at least one of the following: body movement, heartbeat, and breathing of the user.

4. The sleeping state improvement system according to claim 3, wherein
    the environment is ambient temperature of the user, and the control unit gradually lowers the temperature over a first predetermined period of time from sleep onset of the user, and gradually raises the temperature over a second predetermined period of time until sleep offset of the user.

5. The sleeping state improvement system according to claim 1, wherein
the first detection unit detects the individual attribute information by detecting sleep onset of the user and sleep offset of the user based on the biological information, and
the individual attribute information includes at least one of the following: the average sleep duration of the user and the sleep duration of the user during a previous predetermined period of time.

6. The sleeping state improvement system according to claim 1, wherein
the control unit is further configured to determine that the user has reached sleep onset based on that the read-out device read out of the individual attribute information.

7. The sleeping state improvement system according to claim 1, wherein
the individual attribute information includes at least one of the following: sleep depth, body temperature, average sleep duration of the user, and sleep duration of the user during a previous predetermined period of time.

8. The sleeping state improvement system according to claim 1, wherein
the control unit controls the environment during sleep of the user by controlling an air conditioner,
the environment includes an air-conditioned environment, and
the air-conditioned environment includes at least one of the following: temperature of air-conditioned air blown out from the air conditioner, humidity of air-conditioned air blown out from the air conditioner, flow direction of air-conditioned air blown out from the air conditioner, volume of air-conditioned air blown out from the air conditioner, cleanliness of air-conditioned air blown out from the air conditioner, and amount of ventilation provided by the air conditioner.

9. The sleeping state improvement system according to claim 1, further comprising
a second detection unit configured to detect the biological information and further detect sleep onset of the user based on biological information, the second detection unit being located in the second place.

10. A sleeping state improvement system configured to improve a sleeping state of a user, comprising:
a memory device that can be carried by the user from a first place to a second place and configured to store identification information to identify the user, the second place being different from the first place, and the first and second places being places where the user sleeps with the first place being a place where the user usually sleeps;
a first detection unit configured to detect biological information of the user and further detect individual attribute information of the user based on the biological information of the user during sleep of the user in the first place, the first detection unit being located in the first place;
a management device configured to store the individual attribute information detected by the first detection unit and the identification information with the individual attribute information associated with the identification information on the memory device in the first place;
a read-out device configured to read out the identification information from the memory device carried to the second place by the user and further read out the individual attribute information associated with the identification information from the management device, the read-out device being located in the second place; and
a control unit configured to control an environment in the second place during sleep of the user in the second place based on the individual attribute information read out by the read-out device from the memory device carried to the second place by the user, the control unit being located in the second place,
the memory device being configured to communicate with the management device and the read-out device, the memory device being carryable from the first place to the second place without carrying the first detection unit and the management device from the first place to the second place.

11. The sleeping state improvement system according to claim 10, wherein
the read-out device transmits the identification information to the management device via a network and receives the individual attribute information from the management device via the network.

12. The sleeping state improvement system according to claim 11, wherein
the control unit is further configured to determine that the user has reached sleep onset based on that the read-out device received the individual attribute information via the network.

13. The sleeping state improvement system according to claim 10, wherein
the biological information includes information regarding at least one of the following: body movement, heartbeat, and breathing of the user.

14. The sleeping state improvement system according to claim 10, further comprising
a second detection unit configured to detect the biological information and further detect sleep onset of the user based on biological information, the second detection unit being located in the second place.

15. The sleeping state improvement system according to claim 10, wherein
the first detection unit detects the individual attribute information by detecting sleep onset of the user and sleep offset of the user based on the biological information, and
the individual attribute information includes at least one of the following: the average sleep duration of the user and the sleep duration of the user during a previous predetermined period of time.

16. The sleeping state improvement system according to claim 10, wherein
the control unit is further configured to determine that the user has reached sleep onset based on that the read-out device read out of the individual information.

17. A sleeping state improvement method to improve a sleeping state of a user, the sleeping state improvement method comprising:
providing a memory device that can be carried by the user from a first place to a second place different from the first place, the first and second places being places where the user sleeps with the first place being a place where the user usually sleeps;
detecting biological information of the user and individual attribute information of the user based on the biological information of the user during sleep of the user in the first place using a first detection unit in the first place;

storing the individual attribute information detected by the first detection unit on the memory device in the first place using a first write-in device in the first place;

reading out the individual attribute information from the memory device carried to the second place by the user using a read out device in the second place; and controlling an environment in the second place during sleep of the user in the second place based on the individual attribute information read out in the second place from the memory device carried to the second place by the user, the memory device being configured to communicate with the first write-in device and the read-out device, the memory device being carryable from the first place to the second place without carrying the first detection unit and the first write-in device from the first place to the second place.

* * * * *